(12) United States Patent
Nakaji

(10) Patent No.: US 9,345,493 B2
(45) Date of Patent: May 24, 2016

(54) CRANIAL PLATING AND BUR HOLE COVER SYSTEM AND METHODS OF USE

(76) Inventor: Peter Nakaji, Phoenix, AZ (US)

(*) Notice: Subject to any disclaimer, the term of this patent is extended or adjusted under 35 U.S.C. 154(b) by 431 days.

(21) Appl. No.: 13/469,062

(22) Filed: May 10, 2012

(65) Prior Publication Data

US 2012/0289964 A1 Nov. 15, 2012

Related U.S. Application Data

(60) Provisional application No. 61/484,641, filed on May 10, 2011.

(51) Int. Cl.
*A61B 17/68* (2006.01)
*A61B 17/80* (2006.01)
*A61B 17/16* (2006.01)

(52) U.S. Cl.
CPC ........... *A61B 17/1695* (2013.01); *A61B 17/688* (2013.01)

(58) Field of Classification Search
CPC ...... A61B 17/688; A61B 17/68; A61B 17/80; A61B 17/8061; A61B 17/8085; A61B 17/8071; A61B 17/8076
USPC .............................. 606/80, 280–299, 902, 903
See application file for complete search history.

(56) References Cited

U.S. PATENT DOCUMENTS

| | | | | |
|---|---|---|---|---|
| 4,573,458 A | * | 3/1986 | Lower | A61B 17/8085 606/280 |
| 5,201,737 A | * | 4/1993 | Leibinger et al. | 606/284 |
| 5,207,681 A | * | 5/1993 | Ghadjar et al. | 606/96 |
| 5,876,405 A | * | 3/1999 | Del Rio et al. | 606/80 |
| 5,961,519 A | * | 10/1999 | Bruce et al. | 606/280 |
| 6,045,552 A | * | 4/2000 | Zucherman | A61B 17/1604 606/71 |
| 6,093,201 A | * | 7/2000 | Cooper et al. | 606/232 |
| 6,206,885 B1 | * | 3/2001 | Ghahremani et al. | 606/96 |
| RE37,249 E | * | 6/2001 | Leibinger et al. | 606/281 |
| 6,929,646 B2 | * | 8/2005 | Gambale | 606/71 |
| 8,152,809 B1 | * | 4/2012 | Kao et al. | 606/80 |
| 8,435,265 B2 | * | 5/2013 | Konieczynski et al. | 606/246 |
| 2006/0224242 A1 | * | 10/2006 | Swords et al. | 623/17.19 |
| 2007/0173844 A1 | * | 7/2007 | Ralph et al. | 606/72 |
| 2009/0076617 A1 | * | 3/2009 | Ralph et al. | 623/17.19 |
| 2010/0036413 A1 | * | 2/2010 | Nakaji | A61B 17/688 606/213 |
| 2010/0241165 A1 | * | 9/2010 | Konieczynski et al. | 606/248 |
| 2012/0289964 A1 | * | 11/2012 | Nakaji | 606/80 |
| 2013/0226249 A1 | * | 8/2013 | Konieczynski et al. | 606/282 |

* cited by examiner

*Primary Examiner* — Christian Sevilla
*Assistant Examiner* — Eric S Gibson
(74) *Attorney, Agent, or Firm* — Adli Law Group P.C.

(57) ABSTRACT

The present disclosure is for a device, tooling, methods of use and kits containing the cranial plates and bur hole covers used for resecuring a cranial flap after a craniotomy. The cranial repair system is meant to reduce the profile of cranial plates or bur hole covers on the external surface of the cranium after a craniotomy is performed. The embodied devices of present disclosure are designed to reside substantially within the kerf or bur holes and thus minimize the surface area of devices resides on the external surface of the cranium. Additional embodiments include kits, tooling and methods to further reduce and/or eliminate the external profile of the cranial plate on the external cranial surface.

12 Claims, 18 Drawing Sheets

CRANIAL PLATING AND BUR HOLE COVER SYSTEM AND METHODS OF USE

CROSS REFERENCE TO RELATED APPLICATION(S)

This application claims the benefit of priority under 35 U.S.C. §119(e) of U.S. Ser. No. 61/484,641 filed May 10, 2011 the entire content is incorporated herein by reference.

BACKGROUND OF THE INVENTION

1. Field of the Invention

The invention relates generally to cranial closure improvements and more specifically to devices and methods used to improve cranial healing and reconstruction and the decrease in patient discomfort and/or palpable or visible deformities often present after a craniotomy.

2. Background Information

Craniotomy is a common operation in the United States. It is performed for a variety of indications, including head trauma, aneurysm repair, and tumor removal, among others. Most craniotomies are performed by drilling one or more bur holes in the skull down to the level of the dura covering the brain and connecting them with a routing bit on a high-speed drill. The bit pulverizes a tract of bone typically two or more millimeters wide. The space left between the bone edges is called the kerf. At the time of closure, the bone flap is replaced with plates and screws, a specialized compressible closure device, wires, or sutures. All of these present methods leave a gap (shown in FIG. 1) which is either centered (FIG. 1a) or eccentric (FIG. 1b). Current cranial plates, bur hole covers and screw systems are mainly if not entirely affixed on the outer surface of the cranium resulting in palpable and often visible protrusions which provide discomfort if in a place where the scalp moves against the protrusions regularly. Because many craniotomies are performed below the hairline, this often results in gross external deformity. Even for craniotomies located off of the forehead, the palpable or visible deformity (particularly for patients who do not have covering hair) and/or accompanying discomfort from the rubbing is often distressing to the patient.

Unfortunately, a suitable device for assisting cranial reconstruction and decreasing cranial deformities and discomfort has not yet been described. Thus, a need exists for methods and devices capable of assisting the surgeon with improved clinical and procedural outcomes when performing craniotomies.

SUMMARY OF THE INVENTION

The present disclosure generally comprises a cranial closure system, devices and methods of use, tooling and kits for improving cranial closure outcomes by using a device including a cranial plate or a bur hole cover with a minimized cranial surface profile. The devices are substantially inset within the kerf and/or bur hole and thus reduces protrusions on the cranial surface and thus provides a better clinical outcome for the patient. Additional embodiments further reduce cranial protrusions by partially or fully insetting the device in relation to the outer surface of the cranium.

An embodiment of the present invention features a cranial plating device which comprises two attachment wings separated by a keel, wherein the two attachment wings are on opposing sides and ends of the keel. When in use one attachment wing attaches to the cranial flap, and the other attaches to the surrounding cranium. A plurality of the embodied cranial plates may be used alone, or with other known cranial plates to secure the cranial flap back to the cranium. Additional embodiments include various keel attachment wing orientations, such as perpendicular or angled, and keel shapes which are straight, curved or bent. Additional embodiments include the keel being solid or perforated to allow or facilitate bone growth therethrough.

Another embodiment of the present invention features a bur hole cover device which comprises three attachment wings separated connected to arms which extend radially from a center and wherein the general shape of the bur hole cover is circular, wherein the three attachment wings are spaced relatively equidistant around the circle. When in use, if one attachment wing attaches to the cranial flap, then the other two arms attach to the surrounding cranium and vice versa. A bur hole cover may be used alone in cases where only a bur hole access was needed for surgical access, or one or more bur hole covers may be used with a plurality of the embodied cranial plates or with other known cranial plates to secure the cranial flap back to the cranium. Additional embodiments include various arm attachment wing orientations, which are rigid enough to provide the structural support necessary yet are somewhat pliable to allow the user to place in non-uniform environments. The embodied arms extend radially from a bur hole cover center and may have various snaking, zigzag or looping shapes which create cover area surface but allow the arm to be flexed a little or somewhat pliable at the attachment wings. Additional embodiments include the bur hole cover being solid or perforated to allow or facilitate further cranial access or bone growth.

Yet another embodiment of the present invention features a specialized tooling apparatus to create a more precise impression for the placement of the attachment wings of an embodied cranial plating and/or bur hole cover device. The tooling apparatus is made to attach to standard neurosurgical tooling. And a preferred tooling apparatus includes a drill bit attachment and guard mechanism. The drill bit attachment comprises a shaft, cutting head and cylindrical tip for creating a pilot hole. The guard attachment fits over the shaft of the drill bit and the top attaches to the drill the guard prevents the drill from drilling past a certain preset depth. Additionally, the guard comprises protruding posts or an orientation ridge which fit against the bone edge so the cylindrical tip makes the pilot hole a standard distance from the edge of the craniotomy and the cutting head removes a more precise section of bone near the kerf.

Additional embodiments feature methods of using the embodied cranial plating device, one embodied method places the keel portion of the plating device within the kerf and affixes the attachment wings of the device on the outer cranial surface without making an impression in the bone first. An additional embodiment uses readily available neurosurgery tools and with a free-hand technique a perforator or bur hole creator is used to cut away a section of bone to create an impression to place the wings of the cranial plate into the impression and to reduce the cranial profile of the plate on the outer surface of the cranium. Another additional embodiment utilizes an embodied precision tooling apparatus to create precise impressions in depth and orientation to the kerf, and affixation pilot holes to secure an embodied cranial plating device to the cranium resulting in a reduced cranial profile that may allow the entire plating system to be fully inset into the cranium and thus avoiding or minimizing the protrusions typically associated with cranial plate devices.

An additional embodiment features a kit for treating a cranial gap associated with a craniotomy in a subject comprising: a bur hole cover, and/or a plurality of cranial plates, a specialized drill bit, and guidance apparatus; and instructions for use.

BRIEF DESCRIPTION OF THE DRAWINGS

FIG. 4 FIG. 4a shows the cranial flap with the embodied plates attached.

FIG. 13 consists of FIGS. 13A-C wherein

DETAILED DESCRIPTION OF THE INVENTION

A craniotomy is a procedure that is frequently performed for the treatment of neurosurgical conditions and diseases. A craniotomy involves the placement of one or more bur holes (full-thickness holes placed in the skull through to the level of the dura) which are connected with the use of a cutting instrument. This cutting instrument can be manual (e.g. a handheld Gigli saw that cuts using a wire blade) or, more commonly, a high-speed drill with a router attachment (craniotome). At the end of the procedure the bone is usually replaced. When it is replaced, the fixation devices used reside above the cranium surface resulting in deformity of the contour of the skull and distress and/or discomfort to the patient.

The devices and methods contemplated in the present invention are based on providing a neurosurgeon with an effective, rapidly deployable, product with a reduced cranial profile when closing the cranial flap and will partially fill the gap (kerf) made by a craniotomy.

Standard craniotome router bits for cutting the human skull that are commercially available include those made by Medtronic Midas Rex, Anspach, Aesculap, Stryker, Codman, and others. Virtually all leave a channel-shaped trough or gap through the bone whose height is the thickness of bone, length is the perimeter of the desired craniotomy, and the width is 2±2 mm. A pediatric bit may leave a gap that is 1.5 mm+/1 mm. Given that at the time of closure the gap may be all positioned to one side or the other, the gap may be 2-4 mm+1-2 mm. The distinct shape and dimensions of the cranial plate embodied allows it to conform to the dimensions of the kerf, even where the kerf varies in width.

Embodiments in Use

A craniotomy is performed for a neurosurgical procedure as follows: The patient's head is positioned and a line is marked in the scalp. The skin is incised with a scalpel and the scalp is held out of the way with a retractor. The bone is exposed by removing the overlying periosteal layer. A high-speed drill is used to drill a small hole through the bone down to the level of the dura, for example, an 8 mm round hole, shaped like a cylinder. A craniotome drill, which is a side-cutting bit with a footplate guard, is used to cut out a flap of bone. This flap can be of any shape or size. The bone removed by the action of the side cutting bur is typically powdered by the bit and is washed away. The gap that is left is called the kerf. The bone flap is elevated off the dura and set aside. The intracranial portion of the procedure is then completed. At the time of closure the bone flap is resecured to the surrounding bone using plates and screws, a clamping device, wire, or suture, or some equivalent method. The secured bone flap will have around it a surrounding gap, the kerf, which is usually left unfilled. The scalp is closed over the bone, the skin is closed with sutures or staples, and the procedure is completed.

Figure 1A:
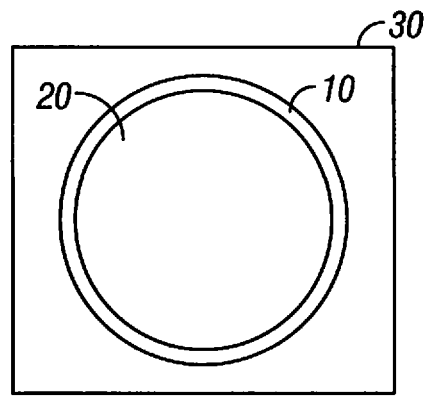
FIG. 1 is a top plan view of a cranium after a craniotomy and consists of FIG. 1a which shows a centered bone flap and FIG. 1b which shows an eccentric bone flap.
Figure 1B:
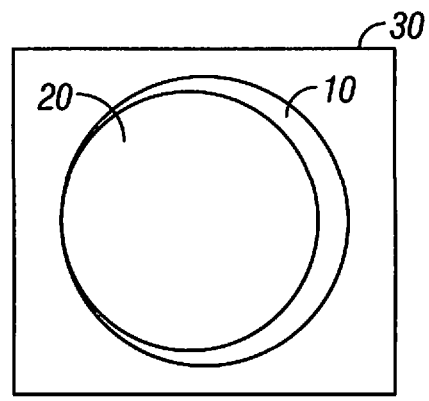

The kerf is a concentric defect in the bone at the time it is created. When the bone flap 20 is replaced, the bone 20 may be replaced in centered fashion (see FIG. 1a), with a kerf 10 of uniform width, or eccentric (see FIG. 1b), with the bone 20 pushed to one side, creating a minimal gap 10 on one side and a wider gap on the other. Placement of the flap eccentrically has advantages in that the presence of bone-to-bone contact on at least one cranial surface 30 will allow the blood supply of the cranium 30 to contact the flap, keeping the bone flap alive and promote fusion of the bone flap 20 to the surrounding bone 30. When the flap 20 is placed eccentrically, the kerf 10 will be tapered at its ends and widest at the middle when viewed from above. The use of a cranial plate that comprises a keel section which resides within the kerf (as shown in FIGS. 2-4) which has at least one of the following features, thin keel material, that is bendable or flexible and is straight, curved or angled from the extending wings, which are placed on opposite sides of the keel and allows the use of the same cranial plate to be used in tight and wide kerfs by simply adjusting the orientation of the device.

Additionally, based on the orientation and features of the embodied cranial plating devices it is possible that less total cranial plates may be necessary to resecure the cranial flap after a craniotomy.

Cranial Plate Designs

Generally, FIGS. 2, 3 and 11 display exemplifications of embodied plates which may feature a straight or curved keel with a perpendicularly oriented wing on either side with each wing facing opposite the other. The wings are designed to accommodate screws to fasten into bone. The plate may or may not have perforations along the length of the keel to allow bone and growth. Additionally the keel may be straight, angled slightly, or curved slightly, and/or the keel may be capable of being bent or adjusted a little bit at time of use. The device may have lateral flex or bend incorporated into the device to assist filling the curved spaces associated with the kerf; or the device may have vertical flex or angle components incorporated into the device to assist the user when dealing with the external curvature of the cranium. Additionally the keel portion which resides in the kerf may be coated with various medicaments and/or healing agents. The keel may be perforated or solid.

Figure 2A:
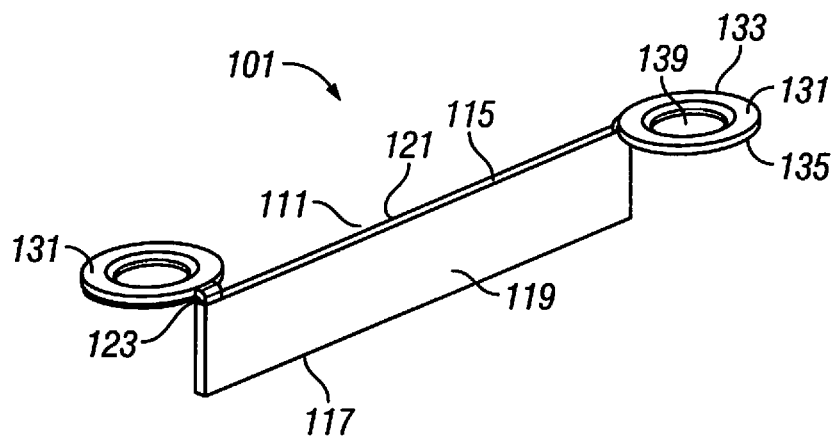
FIG. 2 is a side front perspective view of embodiments of the present invention and consists of FIG. 2a which shows an embodiment wherein the front and back surface of the keel is solid.
FIG. 2b which shows an embodiment wherein the front and back surface of the keel is perforated with circular apertures from front to back.
FIG. 2c which shows an embodiment wherein the front and back surface of the keel is opened with rectangular apertures from front to back.

As demonstrated in more detail in FIG. 2, embodied cranial plates comprise of a keel portion attached to two fixation wings, wherein the fixation wings are on opposite sides and opposite ends of each other. Each of the embodied cranial plates shown in FIG. 2 are shown in a side front perspective view. In the embodied cranial plate 101 shown in FIG. 2a the keel 111 is solid, thus no holes or perforations are visible on the front keel surface 119 or the back keel surface 121 and each fixation wing 131 is attached to the top keel surface 115 at a wing-keel attachment point 123, additionally the keel 111 includes a bottom surface 117 which resides within a kerf 20 (not shown) and is positioned closest to the dura or the brain (not shown) when in use. Each fixation wing 131 has a top surface 133 and a bottom surface 135 and a fixation aperture 139 which extends from the top surface 133 to the bottom surface 135. Typically the fixation aperture 139 is tapered and thus has a wider diameter at the top surface 133 than the bottom surface 135. This tapered fixation aperture 139 is designed to match and closely fit a tapered head fixation device 141 such as a screw (not shown).

Figure 2B:
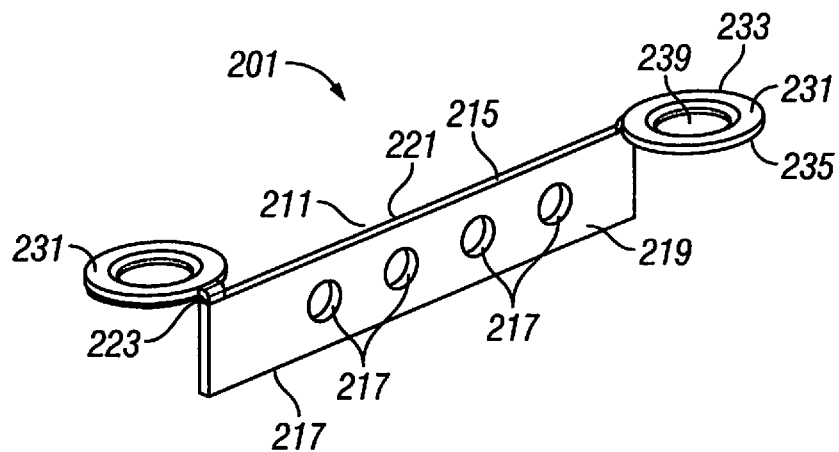

In the embodied cranial plate 201 shown in FIG. 2b the front keel surface 219 and back keel surface 221 of the keel 211 is perforated with circular apertures 225 and each fixation wing 231 is attached to the top keel surface 215 at a wing-keel attachment point 223, additionally the keel 211 includes a bottom surface 217 which resides within a kerf 20 and is positioned closest to the dura or the brain (not shown) when in use. Each fixation wing 231 has a top surface 233 and a bottom surface 235 and a fixation aperture 239 which extends from the top surface 233 to the bottom surface 235. Typically the fixation aperture 239 is tapered and thus has a wider diameter at the top surface 233 than the bottom surface 235. This tapered fixation aperture 239 is designed to match and closely fit a tapered head fixation device 241 such as a screw (not shown).

Figure 2C:
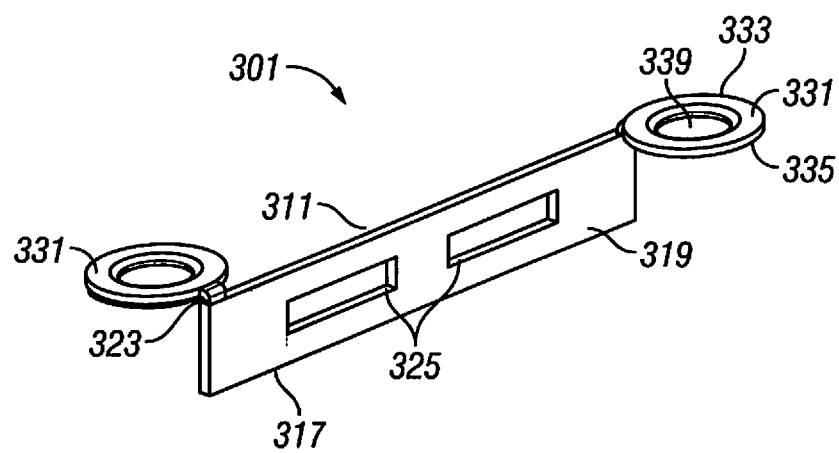

In the embodied cranial plate 301 shown in FIG. 2c the front keel surface 319 and back keel surface 321 of the keel 311 is opened with rectangular apertures 325 and each fixation wing 331 is attached to the top keel surface 315 at a wing-keel attachment point 323, additionally the keel 311 includes a bottom surface 317 which resides within a kerf 20 and is positioned closest to the dura or the brain (not shown) when in use. Each fixation wing 331 has a top surface 333 and a bottom surface 335 and a fixation aperture 339 which extends from the top surface 333 to the bottom surface 335. Typically the fixation aperture 339 is tapered and thus has a wider diameter at the top surface 333 than the bottom surface 335. This tapered fixation aperture 339 is designed to match and closely fit a tapered head fixation device 341 such as a screw (not shown).

As generally discussed above, the keel portion of the cranial plates embodied may have different properties such as being straight or curved, and different orientations in relation to the attachment wings in that the keel may be attached perpendicular to the fixation wings or at an offset angle, additionally each configuration may be created in either a left-handed or right-handed orientation. FIG. 3 is a top plan view of exemplary embodiments of the present invention wherein the orientation and shape of the keel is shown in various designs contemplated in the present invention. In the embodied cranial plate 401 shown in FIG. 3a the keel 411 is not curved and is straight in relation to each fixation wing 431 and each fixation wing 431 is attached to the top keel surface 415 at a wing-keel attachment point 423, wherein the orientation of the keel 411 to each fixation wing 431 is perpendicular.

Figure 3A:
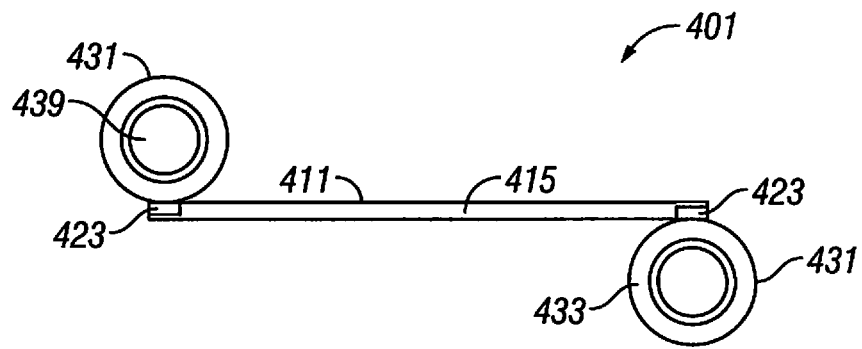
FIG. 3 is a top plan view of embodiments of the present invention and consists of FIG. 3a which shows an embodiment wherein the keel is straight in relation to the wings.
FIG. 3b which shows an embodiment wherein the keel is angled in relation to the wings.
FIG. 3c which shows an embodiment wherein the keel is curved in relation to the wings.
FIG. 3d which shows an embodiment wherein the device shown in FIG. 3c as a right handed configuration is shown in FIG. 3d as a left-handed configuration.
Figure 3B:
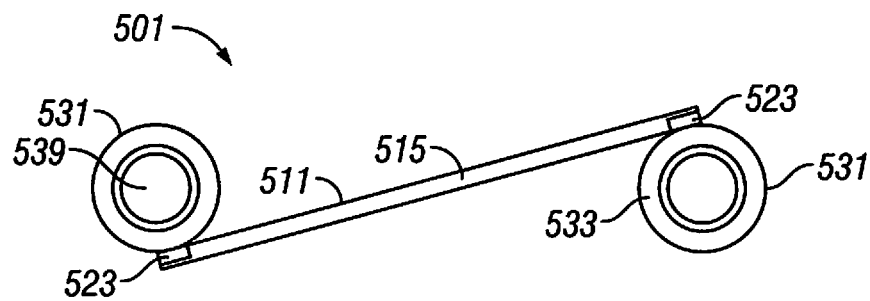

In the embodied cranial plate 501 shown in FIG. 3b the keel 511 is not curved but is angled in relation to each fixation wing 531 and each fixation wing 531 is attached to the top keel surface 515 at a wing-keel attachment point 523, wherein the orientation of the keel 511 to each fixation wing 531 is at an offset angle.

Figure 3C:
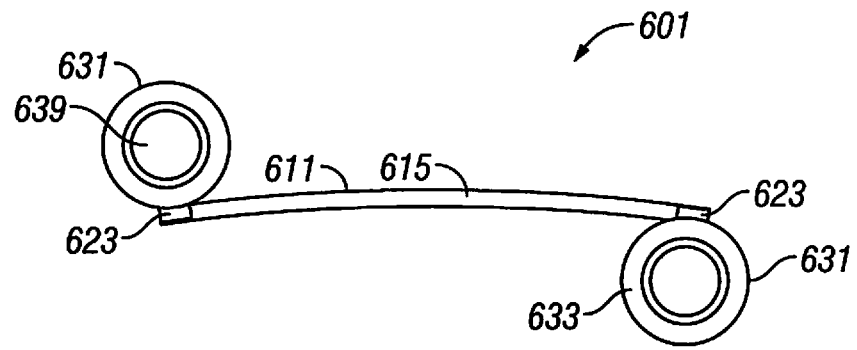
Figure 3D:
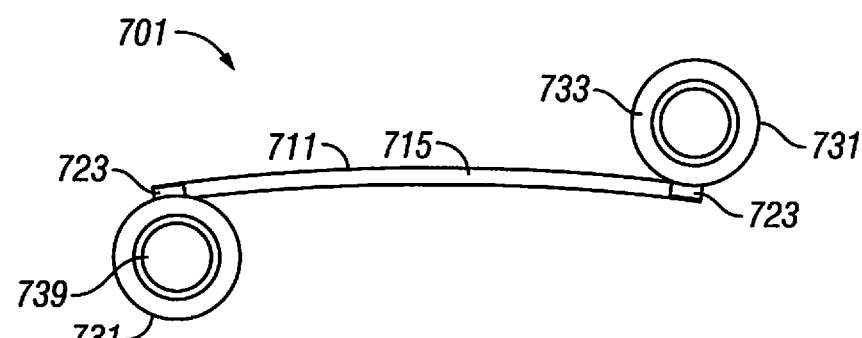

In the embodied cranial plates 601 and 701 shown in FIG. 3c and the d respectively, the keel 611, 711 is curved or bowed slightly in relation to each fixation wing 631, 731 and each fixation wing 631, 731 is attached to the top keel surface 615, 715 at a wing-keel attachment point 623, 723, wherein the orientation of the keel 611, 711 to each fixation wing 631, 731 may be perpendicular (as shown), or at an offset angle. Additionally, the difference between cranial plate 601 in FIG. 3c and cranial plate 701 in FIG. 3d is that cranial plate 601 is in a right handed configuration as shown and cranial plate 701 is in a left-handed configuration as shown.

FIG. 11 comprises of cranial plate designs 11A-11L which further demonstrate a sampling of versatile cranial plates contemplated in the present invention. In the embodied cranial plate 801 shown in FIG. 11A the keel 811 is straight in relation to each fixation wing 831 and each fixation wing 831 is attached to the top keel surface 815 at a wing-keel attachment point 823, and the keel 811 has a shortened depth as measured by the distant from the top keel surface 815 to the bottom keel surface 817 this embodiment may be useful in places where the cranium thickness is less or compromised.

Figure 11A:
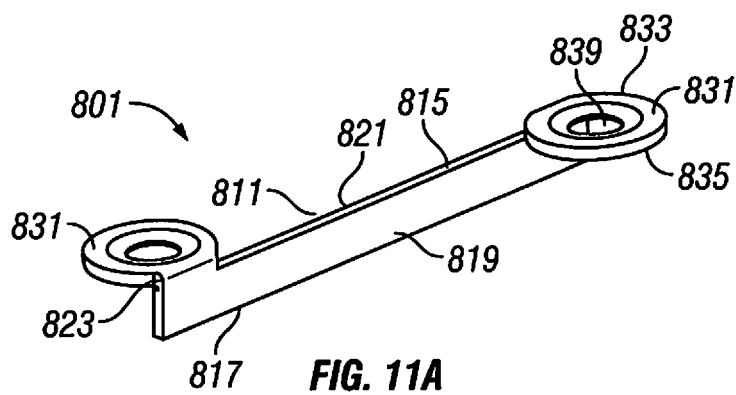
FIG. 11 consists of FIGS. 11A-11L each of which is a perspective view of an embodied cranial plate device.
Figure 11B:
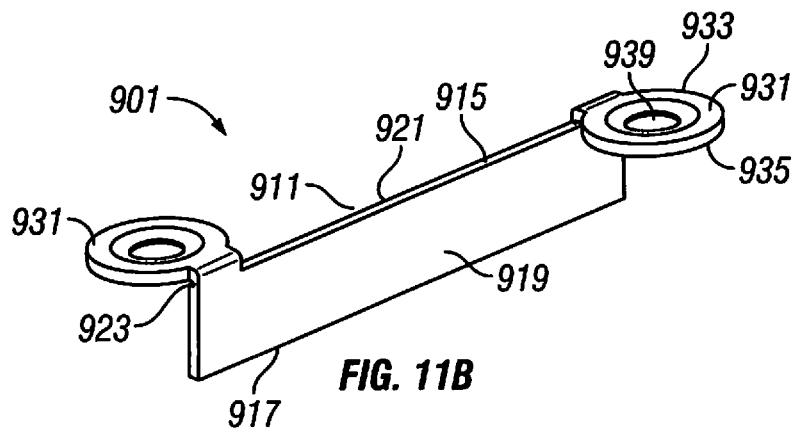

In the embodied cranial plate 901 shown in FIG. 11B the keel 911 is straight in relation to each fixation wing 931 and each fixation wing 931 is attached to the top keel surface 915 at a wing-keel attachment point 923, which is thick to provide greater structural integrity to the device.

Figure 11C:
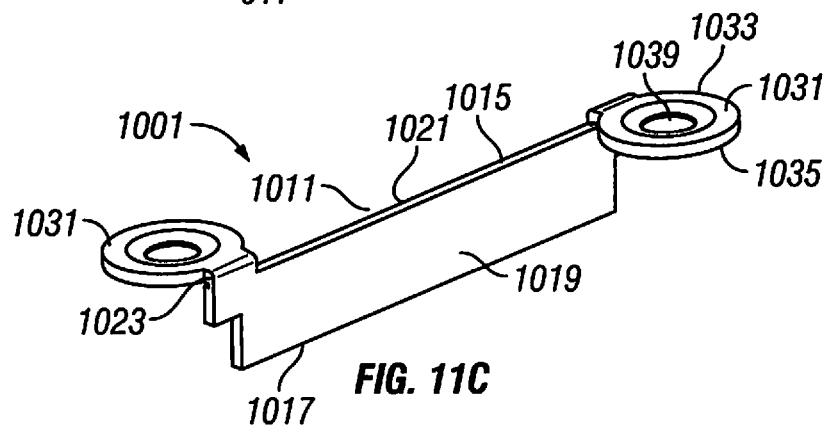
Figure 11D:
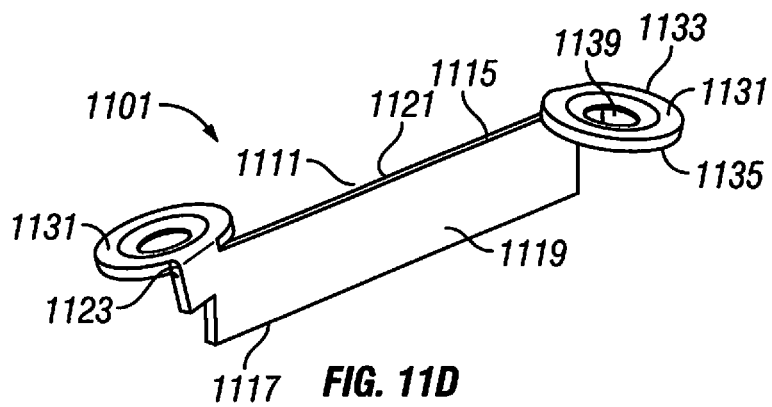

In the embodied cranial plate 1001 shown in FIG. 11C the keel 1011 is straight in relation to each fixation wing 1031 and each fixation wing 1031 is attached to the top keel surface 1015 at a wing-keel attachment point 1023, and the keel 1011 has a shortened depth shelf created by a larger wing-keel attachment point 1023 which enables the plate to fit better in certain kerf arrangements. The embodied cranial plate 1111 shown in FIG. 11D is identical to that shown in 11C with the exception that the larger wing-keel attachment point 1123 is angled downward so that the wing-keel attachment point 1123 is at less than a 90 degree angle in relation to the keel 1111. The angle created is an example of a vertical flex or angle which assists the user when dealing with the external contours of a cranium.

Figure 11E:
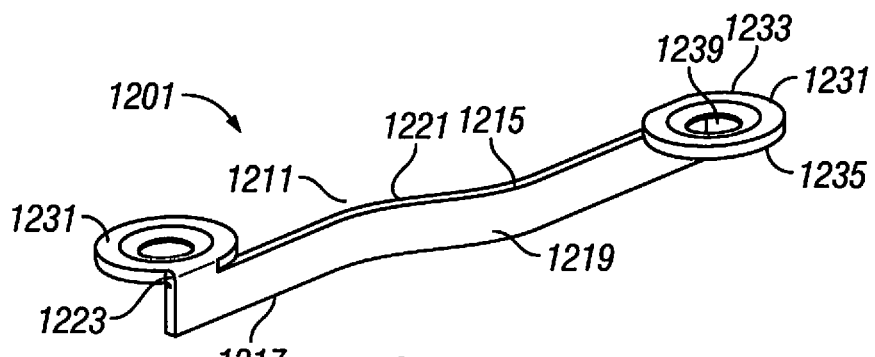
Figure 11F:
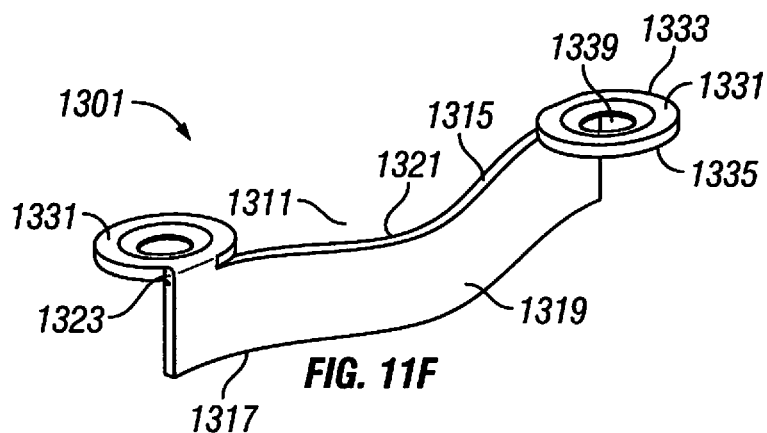

In the embodied cranial plate 1201 shown in FIG. 11E the keel 1211 is angled in a very slight s-formation in relation to each fixation wing 1231 and each fixation wing 1231 is attached to the top keel surface 1215 at a wing-keel attachment point 1223, and the keel has a shallow depth similar to plate 801. In FIG. 11F the cranial plate 1301 has a keel 1311 that is angled in an s-formation like 1201 but in this case the angle is much more pronounced and the keel 1311 is not a shallow depth keel like 1211.

Figure 11G:
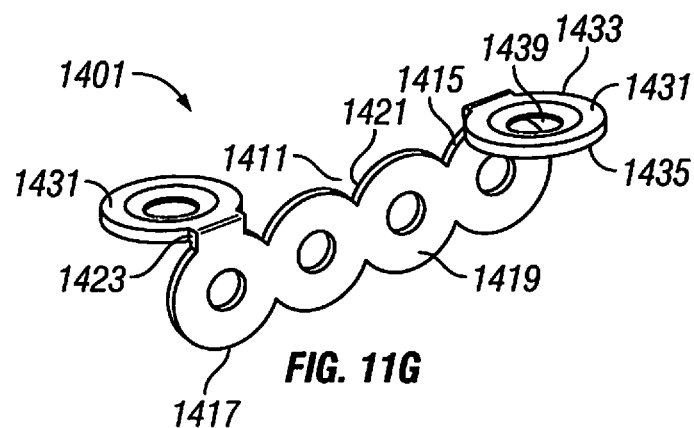
Figure 11H:
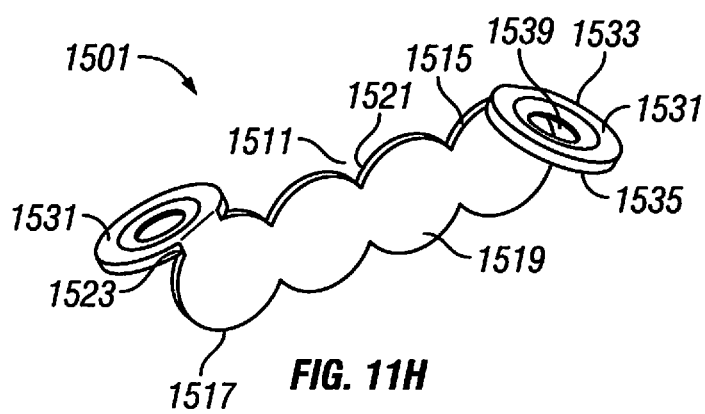

In the embodied cranial plate 1401 shown in FIG. 11G the keel 1411 is straight in relation to each fixation wing 1431 and each fixation wing 1431 is attached to the top keel surface 1415 at a wing-keel attachment point 1423, and the keel 1411 circular chain design and apertures therethrough which may facilitate bone growth. FIG. 11H shows an embodied cranial plate 1501 with a similar circular keel design 1511 as shown in FIG. 11G with the exception that the keel 1511 does not have apertures. Additionally each fixation wing 1531 is attached to the top keel surface 1515 at a wing-keel attachment point 1523 but the wing-keel attachment point 1523 is angled or dog-eared down.

Figure 11I:
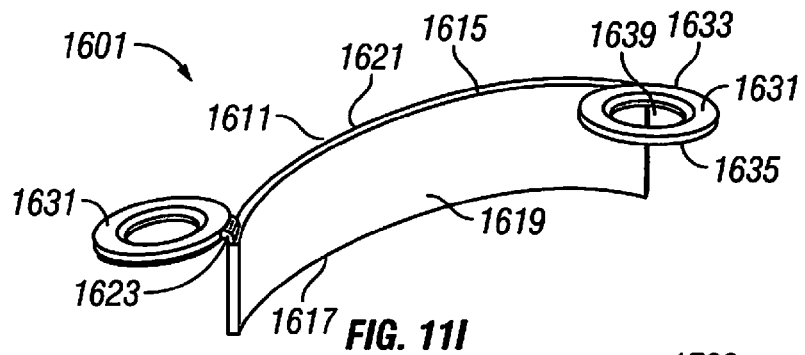
Figure 11J:
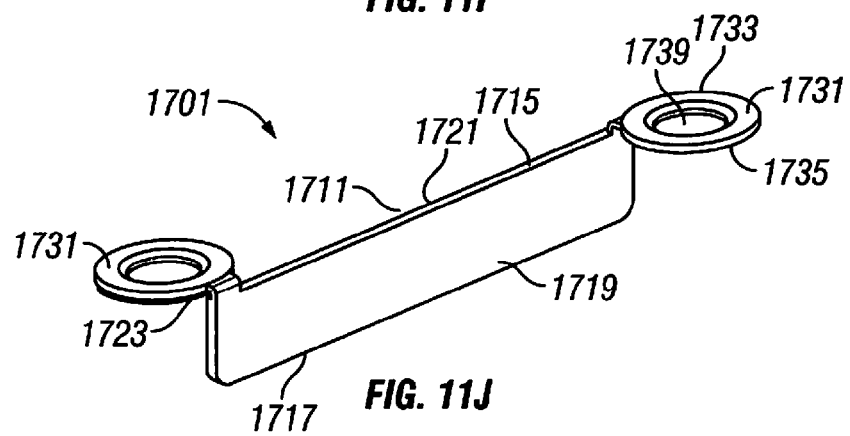
Figure 11K:
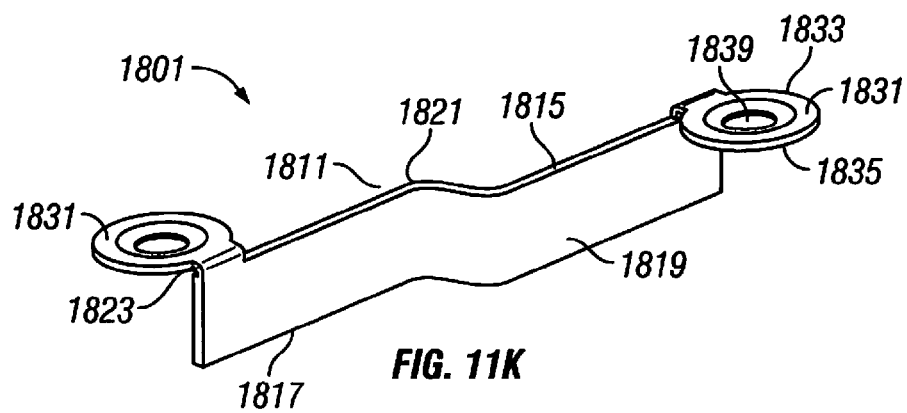
Figure 11L:
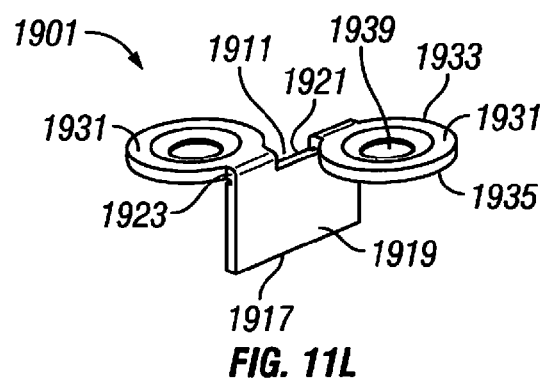

In the embodied cranial plate 1601 shown in FIG. 11I the keel 1611 is angled in a c-curve formation in relation to each fixation wing 1631. In the embodied cranial plate 1701 shown in FIG. 11J the keel 1711 is straight in relation to each fixation wing 1731 but the keel has a tapered or rounded bottom surface 1717. In the embodied cranial plate 1801 shown in FIG. 11K the keel 1811 is angled in a z or zigzag formation in relation to each fixation wing 1831. In the embodied cranial plate 1901 shown in FIG. 11L the keel 1911 is straight in relation to each fixation wing 1931 but the length of the keel 1911 and the subsequent distance between each fixation wing 1931 is short which enables the plate 1901 to fit better in certain kerf arrangements.

Figure 4A:
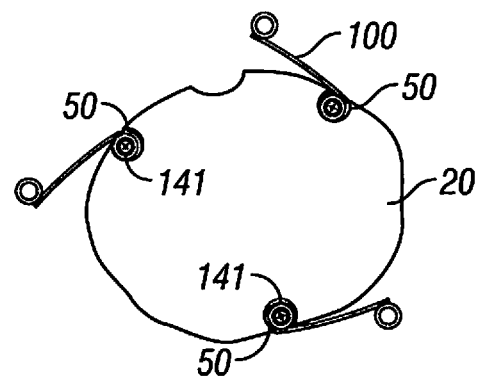
Figure 4B:
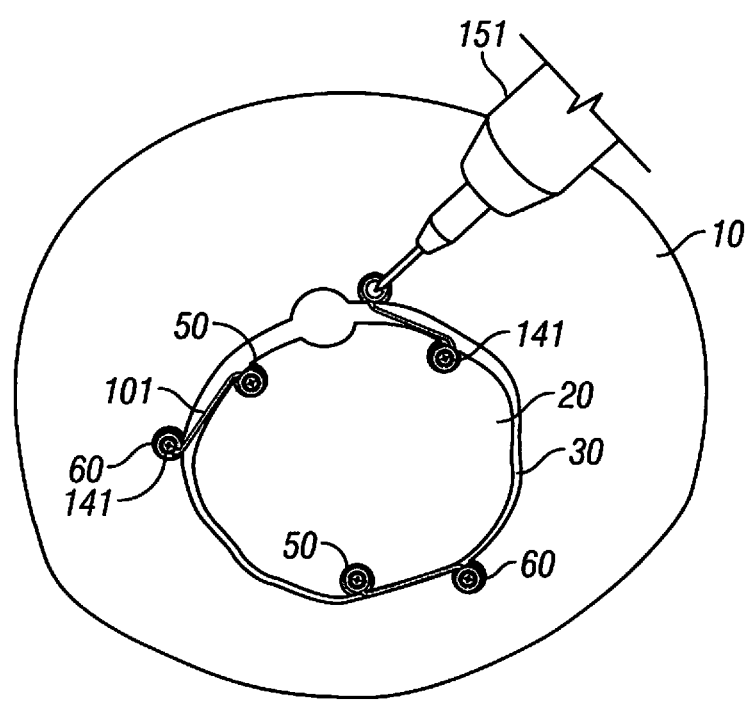
FIG. 4b shows the cranial flap placed back into the cranial opening and being resecured.
Figure 4C:
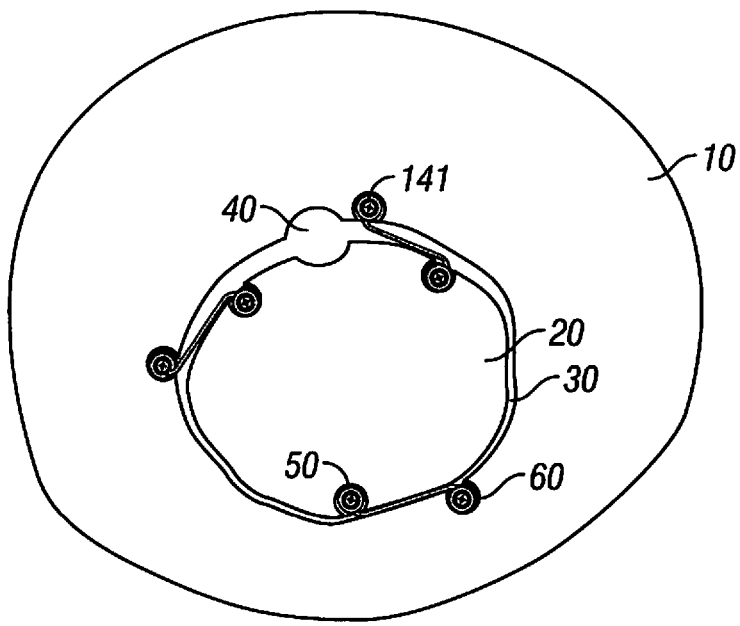
FIG. 4c shows the completed cranial closure with embodied cranial plates.

A demonstration of the application of an embodied cranial plating device 101 into a kerf 10 where the cranial bone flap 20 is centered compared to the outlying cranium 30 is shown in FIG. 4. FIG. 4a demonstrates how one fixation wing 131 of a cranial plate 101 is first placed into a cranial flap wing recess 50 which has been cut away to provide a specific placement of the fixation wing 131 and is adhered to the cranial bone flap 20, with fixation screws 141. FIG. 4b demonstrates the step wherein the cranial flap 20 is oriented back within the cranium 10, using the matching sides of one or more bur holes 40 to provide proper orientation and the keel portion 111 of each device 101 is placed within the kerf 30, and the other fixation wing 131 is placed into the cranium wing recess 60 which has been cut away to provide a specific placement the fixation wing 131 and is adhered to the cranium 10 with fixation screws 141. FIG. 4c demonstrates how the finished procedure appears, wherein a plurality of cranial plates 101 are positioned such that the keel 111 of each plate resides within the kerf 30, and that the fixation wings 131 for each plate 101 are recessed within cranial flap wing recesses 50 or cranium wing recesses 60 such that one wing 131 from each plate 101 is recessed 50 and attached to the cranial flap 20 and the other wing 131 from each plate 101 is recessed 60 and attached to the cranium 10 with fixation screws 141.

Exemplary dimensions of embodied cranial plating devices contemplated in the present invention are as follows: The wings are generally circular but could be a semicircular, oval or trapezoidal shape in alternative embodiments. The diameter of the wings are usually the same but could be different in certain embodiments for example, where it is advantageous to have a smaller fixation wing on the cranial plate then on the cranium. The diameter of the wings may be from about 2 mm to about 8 mm, with a preferred diameter from about 3 mm to about 5 mm with a diameter of about 4 mm being most preferred. The depth of the wings is from about 0.1 to about 2.0 mm, with a preferred depth of about 0.2 to 0.8 mm and most preferred about 0.5 to 0.6 mm. The affixation aperture within the wing may be tapered or untapered. Although tapered is preferred and used in conjunction with matching tapered affixation screws. The top width of the affixation aperture is about 1.5 to 4 mm, with a preferred top width of 1.7 to 3.0 mm and most preferred about 2 mm. The bottom width of the affixation aperture is about 0.1 to about 2.0 mm, with a preferred width of about 0.2 to about 1.5 mm, and a most preferred width of about 1.0 mm. The affixation screws preferred are size 2-8 mm affixation screws with size 3-4 mm affixation screw most preferred. The size of the affixation screws are chosen by the neurosurgeon based on the thickness of the bone at the point of use. The keel portion of an embodied cranial plate may have a depth (length from top of keel portion which interfaces with the fixation wings located on the outer cranial side to the bottom of the keel located towards the dura or brain) ranging from 1-10 mm, with a preferred depth from 2-7 mm and the most preferred depth of about 4 mm. The keel length contemplated may range from about 6-20 mm, with a preferred length of 8-15 mm, and the most preferred length of 10-12 mm. The contemplated keel widths may be the same from top to bottom when in rectangular form or will have a greater top width than bottom width when the keel is tapered in width. The contemplated keel widths for either tapered or rectangular embodiments range from a top width of 0.1 to about 2 mm with a preferred width of 0.2 to about 1.0 mm and a most preferred top width of about 0.5 mm for untapered widths and 0.6 mm for tapered widths. The bottom width ranges from of 0.1 mm to 2.0 mm with a preferred width of 0.3 mm to 0.6 mm and a most preferred bottom width of 0.4 mm to 0.5 mm. This matches the contemplated kerf widths of about 1-5 mm in an adult and 1-4 mm in pediatric procedures.

Additional embodiments of the present disclosure include a method for improving the clinical outcome of a craniotomy comprising: reducing the protrusions associated with current cranial plating systems and reducing the indentations or gaps left in the bone following a craniotomy; wherein said indentations or gaps are filled with the keel portion of an embodied cranial plating device.

Additional embodiments of the cranial plating device can include:

Embodiments where the keel may be coated or provide a scaffold for attachment and/or distribution of analgesics, antibiotics, antibacterial agents, or antiseptic agents in order to prevent or reduce patient discomfort and/or bone flap infection.

Embodiments where the keel may be coated or provide a scaffold for attachment and/or distribution of biological growth factors in order to promote bone growth and ingrowth, such as via osteogenesis, osteoconduction, and/or osteoinduction.

Embodiments where the keel can serve as a scaffold to hold a paste, gel, or other moldable or pourable liquid for the purpose of hardening the bone into a solid matrix to create a hard surface or a watertight seal.

Tooling Embodiment Designs

The tooling system may comprise of a high-powered drill and an impression device which consists of a cylindrical or disc-like bur (drill-bit) and a surrounding guide, the drill-bit is meant to be applied end on into the bone to make a semicircular depression in the bone comprising a ⅗ to almost one whole circle that has a central point to allow the bit to bite bone at a precise spot this will also serve to create a pilot hole for an fixation screw when the plate is applied. The surrounding guide orients the drill-bit into the proper positioning in relation to the bone edge and also may control and/or limit the depth in which the drill-bit may cut into the bone.

Figure 5A:
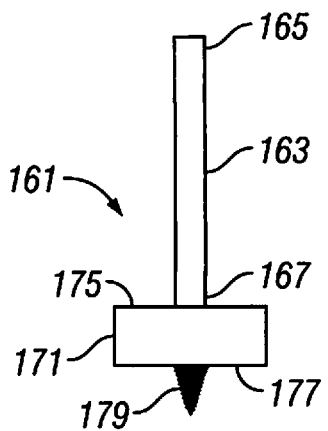
FIG. 5 is a side plan view of a drill-bit tooling embodiment of the present invention and consists of FIG. 5a and FIG. 5b which respectively, show the front side and bottom side of a drill-bit contemplated.
Figure 5B:
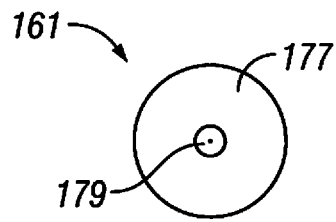

Embodiments of contemplated features of the tooling system are shown in FIGS. 5-7. FIG. 5 is a side plan view of a drill-bit tooling embodiment 161 of the present invention and consists of FIG. 5a and FIG. 5b which respectively, show the front side and bottom side of a drill-bit contemplated in the present disclosure. FIG. 5a shows an embodied cutting drill-bit 161 which comprises a shaft portion 163 which has an upper end 165 which attaches to the drill or perforator tool 155 (not shown) and a lower end 167 which attaches to a cutting bit 171, at the upper surface 175 of the cutting bit 171. The cutting bit 171 also has a bottom cutting surface 177 which is used cut away the bone and make the recesses for the wings of the cranial plates. Attached to the bottom cutting surface 177 is a pilot hole bit 179 which drills a pilot hole 70 (not shown) which orients and directs the proper placement of a cranial plate 101, when the fixation screws 141 (not shown) are screwed into a pilot hole 70 (not shown). FIG. 5b shows the bottom cutting surface 177 of the cutting bit 171 and shows the placement of the pilot hole bit 179 in the center of the bottom cutting surface 177.

Figure 6A:
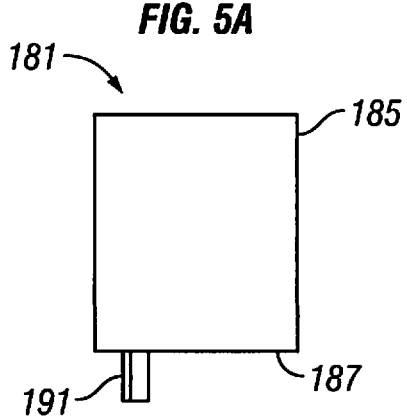
FIG. 6 is a side plan view of a drill-bit guard tooling embodiment of the present invention and consists of FIG. 6a and FIG. 6b which respectively, show the front side and bottom side of a drill-bit guard contemplated.
FIG. 6c and FIG. 6d which respectively, show the front side and bottom side of an alternative drill-bit guard contemplated.
Figure 6B:
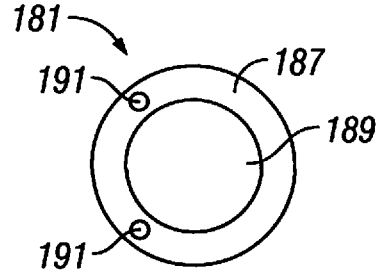
Figure 6C:
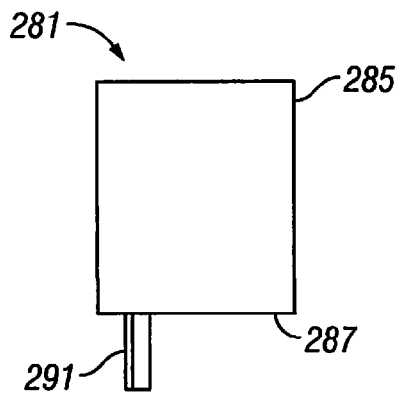
Figure 6D:
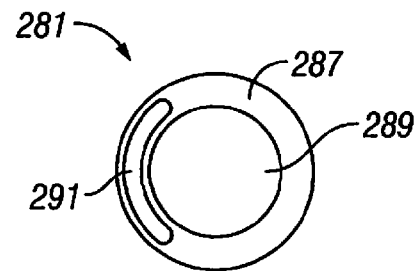

FIG. 6 is a side plan view of a drill-bit guard tooling embodiment 181 of the present invention and consists of FIG. 6a and FIG. 6b which respectively, show the side and bottom surface of a drill-bit guard contemplated; and FIG. 6c and FIG. 6d which respectively, show the side and bottom surface of an alternative drill-bit guard 281 contemplated. FIG. 6a shows the side view of a guard 181 contemplated, the guard 181 has an upper end 185 which interfaces with the drill or perforator tool 155 (not shown), and controls the depth that a cutting drill-bit 161 can cut by having the upper surface 185 fixed or stopped at a certain drill depth, and the bottom surface 187 which interfaces with the bone to be cut does not allow the cutting bit 171 to drill deeper than where the bottom surface 187 of the guide 181 surrounds the cutting bit 171. Additionally the guide has two protruding orientation posts 191 which extend from the bottom surface 187 of the guide 181. FIG. 6b further shows the bottom surface 187 of the embodied guide 181 and the relation of the orientation posts 191 on the bottom surface 187. Additionally there is a drill-bit clearance space 189 that is an aperture so that a drill-bit 161 and particularly the cutting bit portion 171 can spin freely within the clearance space 189 without impedance from the guide 181.

FIG. 6c shows the side view of a guard 281 contemplated, the guard 281 has an upper end 285 which interfaces with the drill or perforator tool 155 (not shown), and controls the depth that a cutting drill-bit 161 can cut by having the upper surface 285 fixed or stopped at a certain drill depth, and the bottom surface 287 which interfaces with the bone to be cut does not allow the cutting bit 171 to drill deeper than where the bottom surface 287 of the guide 281 surrounds the cutting bit 171. Additionally the guide has an orientation ridge 291 which extends along the bottom surface 287 of the guide 281 from about the seven o-clock to about the 11 o-clock position. FIG. 6d further shows the bottom surface 287 of the embodied guide 281 and the relation of the orientation ridge 291 along the bottom surface. Additionally there is a drill-bit clearance space 289 that is an aperture so that a drill-bit 161 and particularly the cutting bit portion 171 can spin freely within the clearance space 289 without impedance from the guide 281.

Figure 7A:
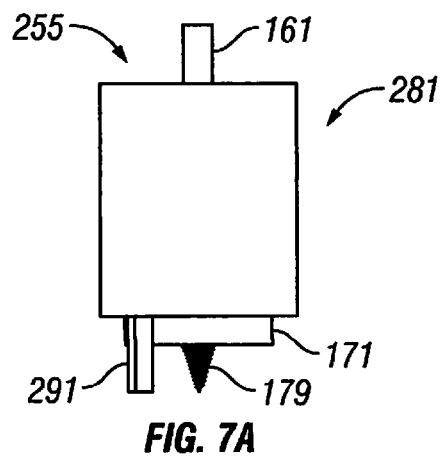
FIG. 7 is a side plan view of a drill-bit with guard tooling embodiment of the present invention and consists of FIG. 7a and FIG. 7b which respectively, show the front side and bottom side of a drill-bit with guard tooling embodiment contemplated.
FIG. 7c and FIG. 7d which respectively, show the front and bottom surfaces of an alternative drill-bit and guard tooling embodiment contemplated.
Figure 7B:
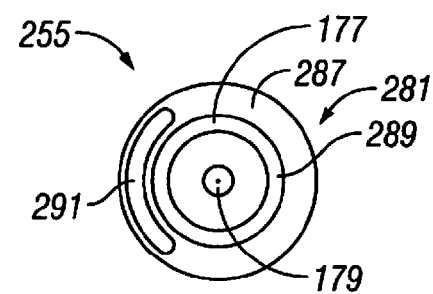

FIG. 7 is a side plan view of a complete specialized cranial plate tooling apparatus 255 with a drill-bit 161 and a guard tooling embodiment 281 of the present invention and consists of FIG. 7a and FIG. 7b which respectively, show the side and bottom surface of the complete apparatus 255 and shows a drill-bit 161 nested within the drill-bit clearance space 289 with-in the guard tooling embodiment 281; FIG. 7b shows the bottom surface 287 of the embodied guide 281 and the relation of the orientation ridge 291 along the bottom surface 287 and in relation to the bottom cutting surface of the bit 177 and the pilot hole cutting bit 179.

Figure 7C:
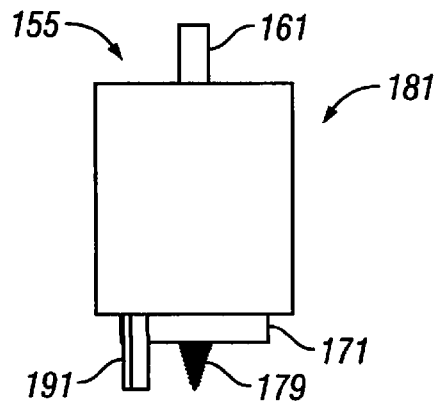
Figure 7D:
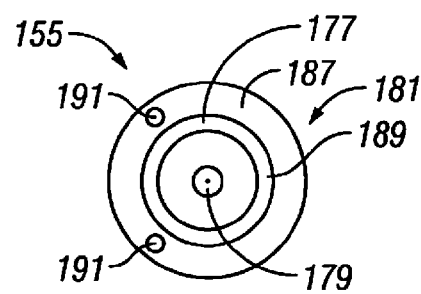

FIG. 7 further includes FIG. 7c and FIG. 7d which respectively, show the side and bottom surface of an alternative complete apparatus 155 and FIG. 7c shows a drill-bit 161 nested within the drill-bit clearance space 189 with-in the guard tooling embodiment 181; FIG. 7d shows the bottom surface 187 of the embodied guide 181 and the relation of the orientation posts 191 along the bottom surface 187 and in relation to the bottom cutting surface of the bit 177 and the pilot hole cutting bit 179.

Exemplary dimensions of an embodied cranial plate tooling apparatus contemplated in the present invention are as follows: The bit portion comprises a head with a diameter of about 2 to about 8 mm, with a preferred diameter from 3-7 mm and the most preferred diameter of about 4 mm. The bit may have a depth of about 0.3 to about 2 mm, but the placement of the guard at a specific depth will restrict the usable depth of the bit to the designated depth for creating the impression in the cranium. This depth ranges from about 0.2 to about 1.0 mm, with a preferred depth of about 0.3 to about 0.8 mm and a most preferred depth of about 0.6 mm. Additionally, the bit comprises a pilot hole bit which may be about 0.5 mm to about 2 mm in diameter and preferred at 1 mm in diameter and 0.5 to 3.0 mm deep, with a preferred depth of about 2 mm. The guard portion of an embodied tooling apparatus has a diameter slightly larger than the diameter of the head of the bit, so that the head can spin unobstructed within the guard. The guard orientation posts may by about 1 to 6 mm long, with a preferred depth of 3 mm.

Figure 8A:
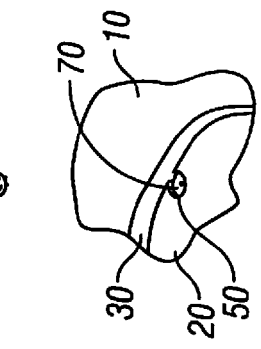
FIG. 8 is a top perspective view showing the use of a drill-bit with guard tooling embodiment to create a recessed fixation point on the cranial flap so that the wings of an embodied cranial plate can be nested and secured and consists of FIGS. 8a, 8b, and 8c which represent a tooling embodiment used on the cranial flap, before cutting (FIG. 8a) during cutting (FIG. 8b) and after cutting (FIG. 8c).
Figure 8B:
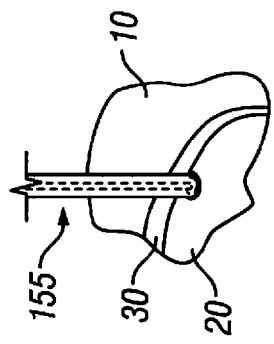
Figure 8C:
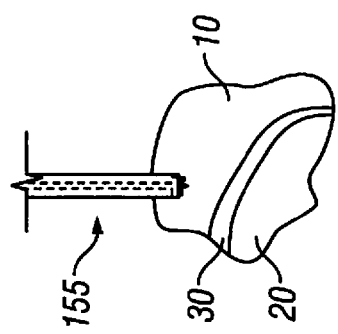
Figure 9A:
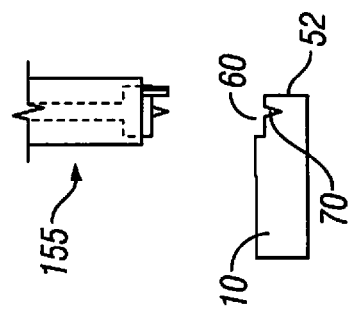
FIG. 9 is a side plan view showing the use of a drill-bit with guard tooling embodiment to create a recessed fixation point on the cranium or cranial flap so that the wings of an embodied cranial plate can be nested and secured and consists of FIGS. 9a, 9b, 9c and 9d which represent a tooling embodiment used on the cranium surface, before cutting (FIG. 9a) during orientation and engagement of pilot hole bit (FIG. 9b) when the cutting tool reaches the depth preset by the guide (FIG. 9c) and after cutting (FIG. 9d).
Figure 9B:
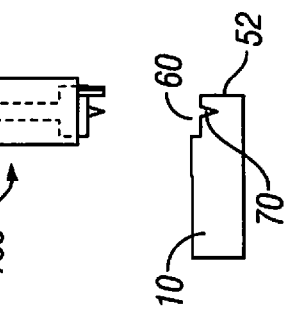
Figure 9C:
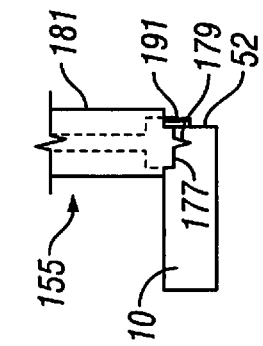
Figure 9D:
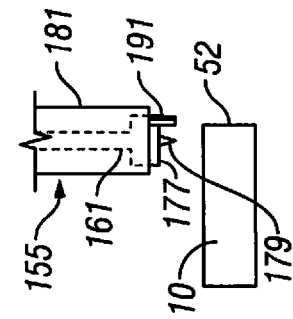
Figure 10A:
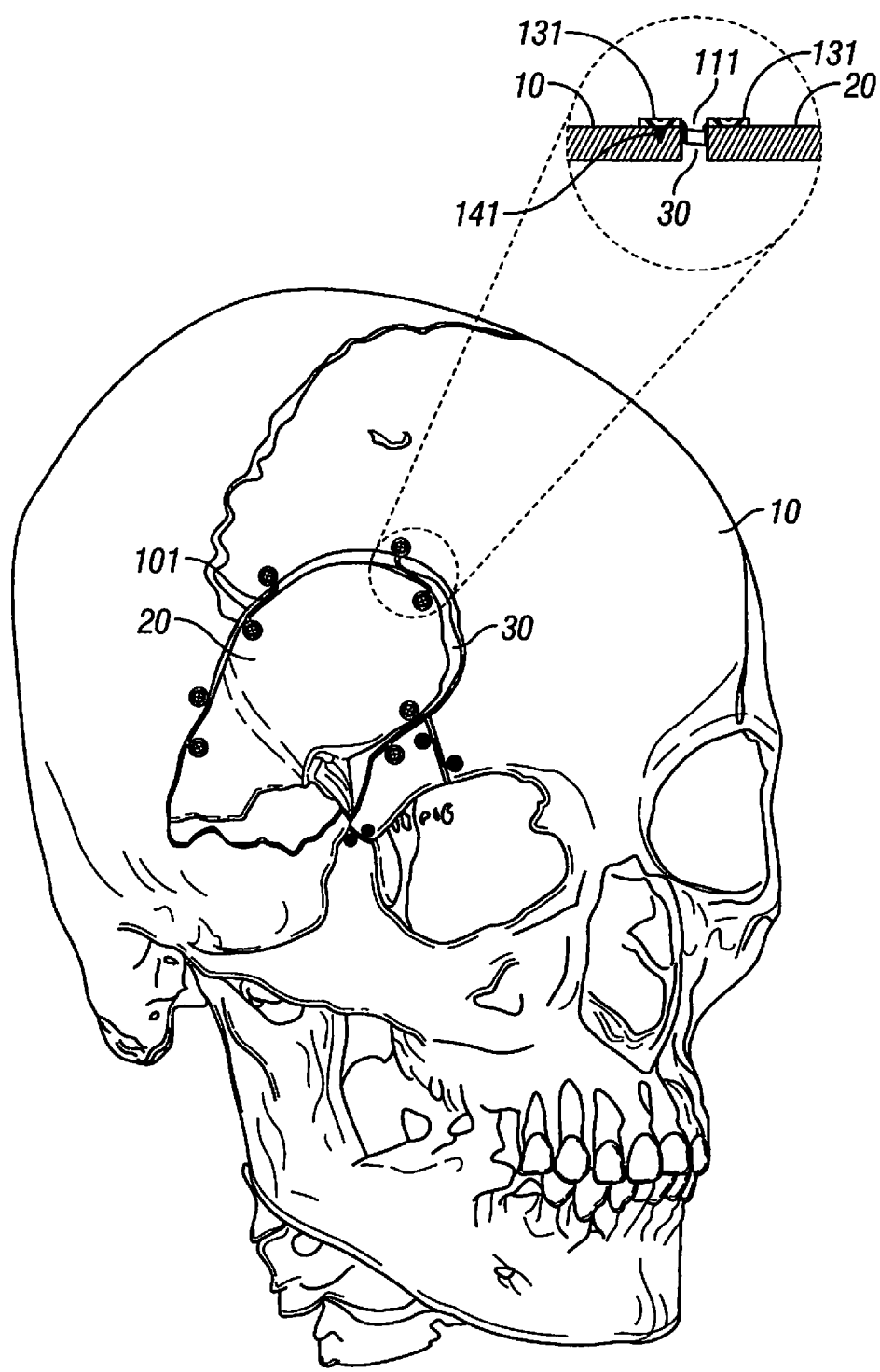
FIG. 10 is a side perspective view of the cranium and embodied cranial plates after attachment and consists of FIG. 10a which shows a cranial plate secured to the cranium like standard plates (thus embedding only the keel within the kerf and the wings are protruding on the cranial surface, FIG. 10b which shows the plate partially embedded as if the embedding process was created free-hand with a perforator only.
FIG. 10c shows the plate embedded in a zero-profile or fully embedded relationship with the cranium as if the embedding process was created with the precision of the embodied tooling components.
Figure 10B:
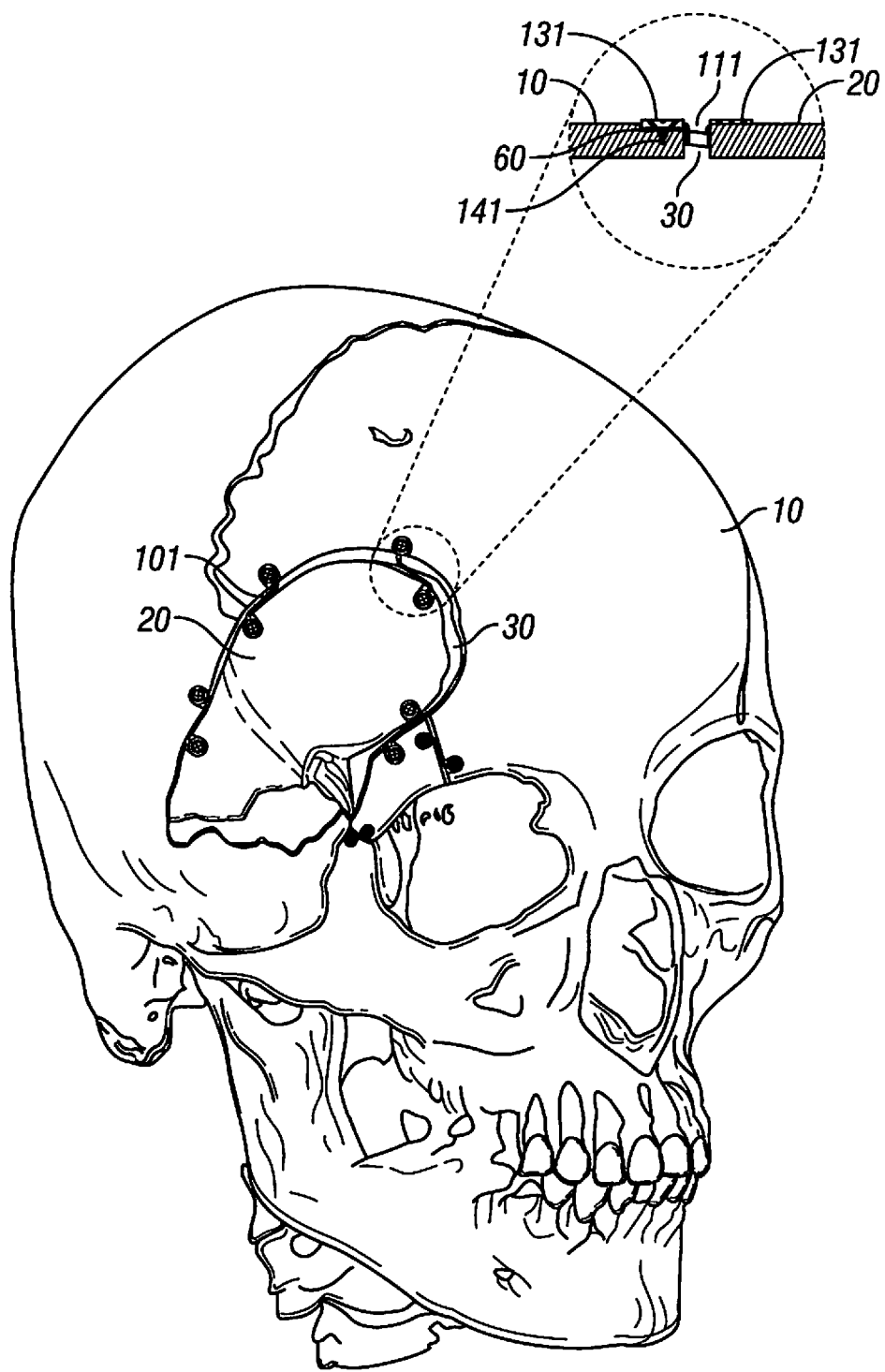
Figure 10C:
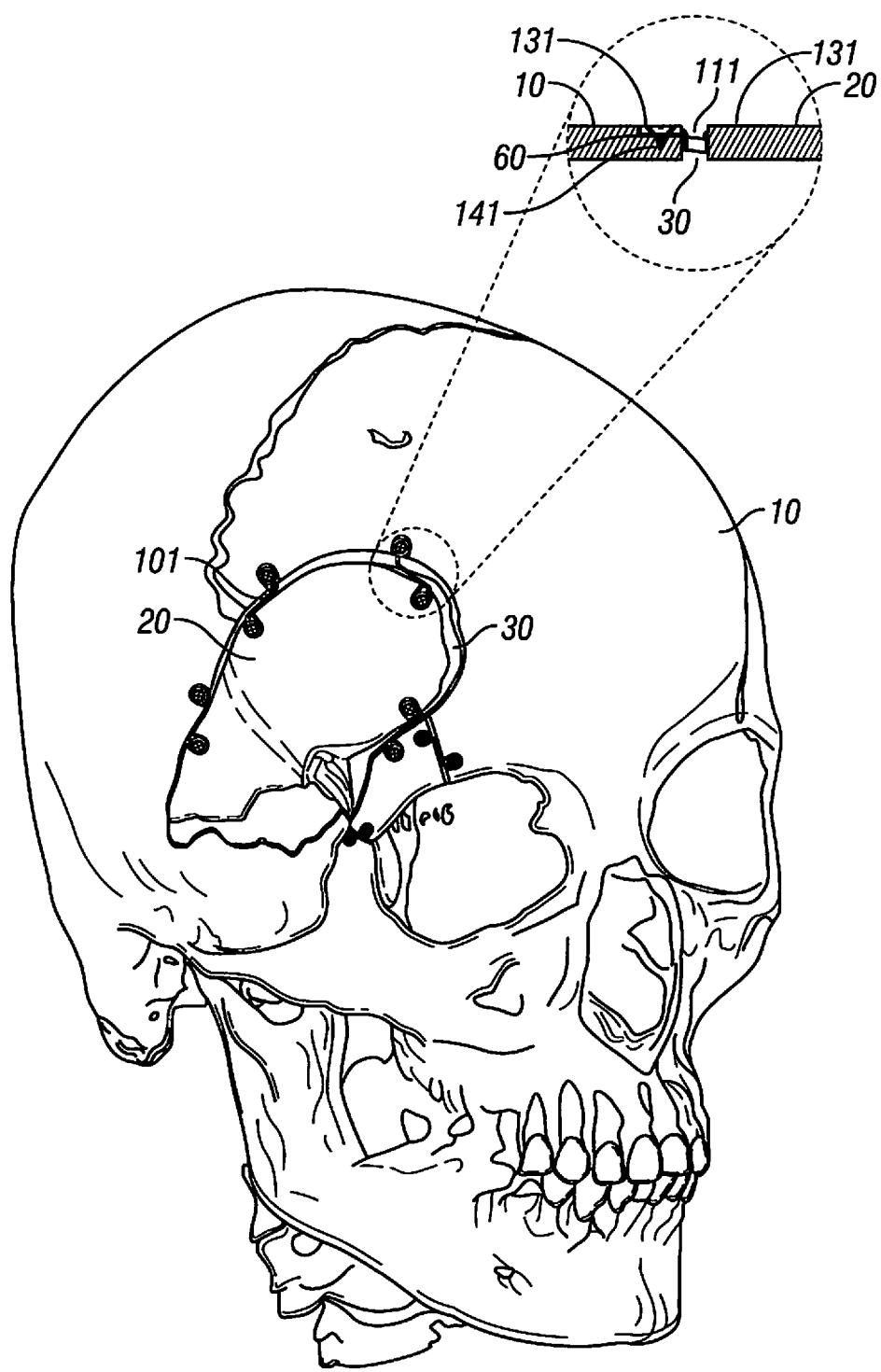

FIGS. 8-10 provide visual exemplifications of how the cranial plates and tooling systems embodied are used to produce a lower profile cranial plate when securing the cranial flap back to the cranium. FIG. 8 comprising FIGS. 8a, 8b, and 8c show a top perspective view showing the temporal use of a complete tooling apparatus 155 to create a recessed fixation point 50 and fixation screw pilot hole 70 on the cranial flap 30. FIG. 8a shows the cranium 10, cranial flap 20 and the kerf 30 awaiting the placement of a cranial plate 101 following surgery. FIG. 8b shows the use of tooling apparatus 155 on the cranial flap 20 while drilling a recessed fixation point 50 and a fixation screw pilot hole which are visible in FIG. 8c.

FIG. 9 is a side plan view showing the use of a complete tooling apparatus 155 including a drill-bit 161 with guard 181 tooling embodiment to create a recessed fixation point on the cranium 60 or cranial flap 50 so that the wings 131 of an embodied cranial plate 101 can be nested and secured and consists of FIGS. 9a, 9b, 9c and 9d which represent the time sequence of the methods when using a tooling apparatus 155 on the cranium surface. FIG. 9a shows the use of the tooling apparatus 155 when preparing to orient the tool 155 to the cranium 10, the user lines the orientation posts 191 up with the bone end 52 before cutting. FIG. 9b shows the tooling apparatus 155 beginning engagement with the cranium bone 10, the orientation posts 191 are flush against the bone end 52 and the pilot hole bit 179 is just starting to drill into the cranium 10. FIG. 9c shows the time when the cutting tool 155 reaches the depth preset by the guide 181 the bottom surface 177 of the guide 181 rests on the cranium 10 and does not allow the apparatus 155 to continue drilling deeper. FIG. 9c shows the result after using the tooling apparatus 155 a cranium recess 60, and fixation screw pilot hole 70 are placed in a uniform position from the bone edge 52.

FIG. 10 is a side perspective view of the cranium and embodied cranial plates after attachment and consists of FIG. 10a which shows a cranial plate 101 secured to the cranium 10 like standard plates. The exploded view portion demonstrates the orientation of the keel 111 within the kerf 30 but the protrusion of the wings 131 when attached to the cranium 10 and flap 20 is evident when seen from this side view. FIG. 10b shows the plate 101 partially embedded in recesses created free-hand with a perforator only. The exploded view portion, shown from the side view, demonstrates the orientation of the keel 111 within the kerf 30 but the protrusion of the wings 131 when attached to the cranium 10 and flap 20 is still evident even though the protrusions of the wings 131 is not as pronounced because a uniform and accurate recess is very difficult to achieve free-hand. FIG. 10 shows the plate 101 embedded in a zero-profile or fully embedded relationship with the cranium as if the embedding process was created with the precision of the embodied tooling components. The exploded side-view portion shows how the wing is embedded in the cranium 10 at a recess point 60, because of the zero-profile of being fully embedded it is not possible to see the cranial flap 20 recess point 50 and fixed wing 131 because the entire cranial plate device 101 resides even with or slightly below the external surface of the cranium.

Bur Hole Cover Designs

Generally, FIG. 12 displays 5 exemplifications (FIGS. 12A-E) of embodied bur hole covers which may feature various arrangements of three arms extending from a center cover portion with attachment wings near the distal end of the arms. The wings are designed to accommodate screws to fasten into bone. The bur hole cover may or may not have perforations along in the center portion or arms to allow brain access or to allow for bone and future growth. Additionally, the arms are meant to cover as much surface area as possible through a combination of any of serpentine, winding, zigzagging, or looping, arrangements in relation to the center portion. The arms must also be thin enough to allow them to be somewhat pliable by the user so that they can make adjustments of the wing placement when attaching the covers to the cranium or a cranial flap. The wing dimensions and attachment methods and tooling may include the same as that described above for the cranial plates and the wing components and properties. The cover may be used in addition with cranial plates during a procedure with a cranial flap, or the cover may be used alone when only a bur hole is drilled for the procedure.

As demonstrated in more detail in FIG. 12, embodied bur hole covers comprise of a center cover portion with three arms extending therefrom to which are attached three fixation wings, wherein the fixation wings dispersed around the perimeter of the substantially circular device. Additional embodiments feature the fixation wings about equidistant from each other. Each of the embodied bur hole covers shown in FIG. 12 are shown in a top plan view. In the embodied bur hole cover 2001 shown in FIG. 12A the center cover portion 2024 is solid, thus no holes or perforations are visible on the surface. Each arm 2022 starts from the center cover portion 2024 and extends radially outward. Each arm 2022 further includes a each fixation wing 2031 in this embodiment the fixation wing 2031 is located at the distal end of the arm 2022. Each fixation wing 2031 has a top surface 2033 and a bottom surface 2035 and a fixation aperture 2039 which extends from the top surface 2033 to the bottom surface 2035. Typically the fixation aperture 2039 is tapered and thus has a wider diameter at the top surface 2033 than the bottom surface 2035. This tapered fixation aperture 2039 is designed to match and closely fit a tapered head fixation device 2041 such as a screw (not shown).

Figure 12A:
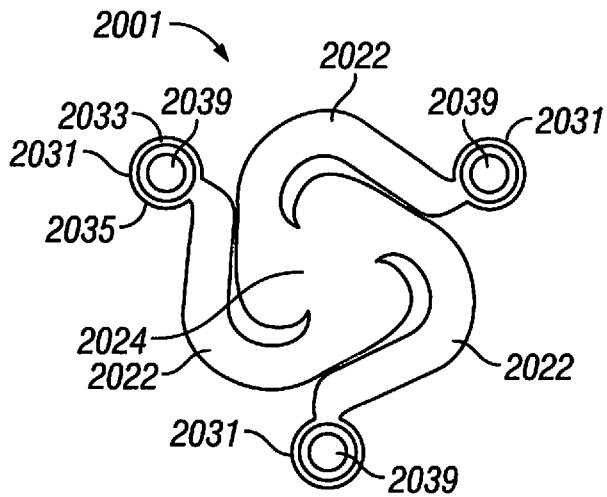
FIG. 12 consists of FIGS. 12A-E each of which is a top plan view of an embodied bur hole cover device.
Figure 12B:
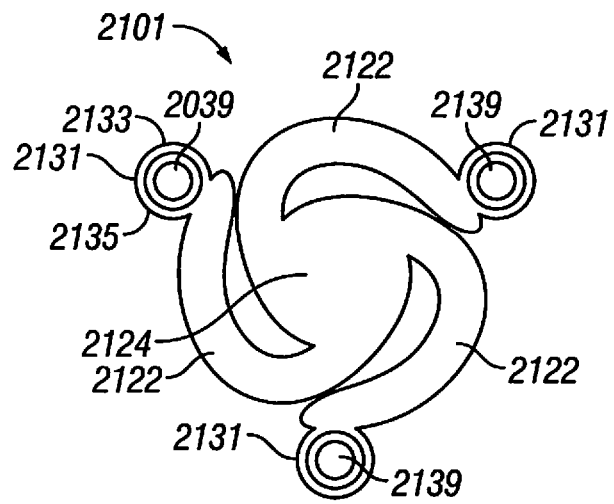

In the embodied bur hole cover 2101 shown in FIG. 12B the center cover portion 2124 is solid and relatively large in that it covers more surface area. Each arm 2122 starts from the center cover portion 2124 and extends radially outward. Each arm 2122 further includes a each fixation wing 2131 in this embodiment the fixation wing 2031 is located closer to the center cover portion so that although near the distal end of the arm 2022 it is not located at the very distal end. Embodiments contemplated allow for the fixation wing 2131 to be located at various points along the arm 2122 as long as some flex or give is available to the user when securing the fixation wings 2131 to the cranial flap or cranium.

Figure 12C:
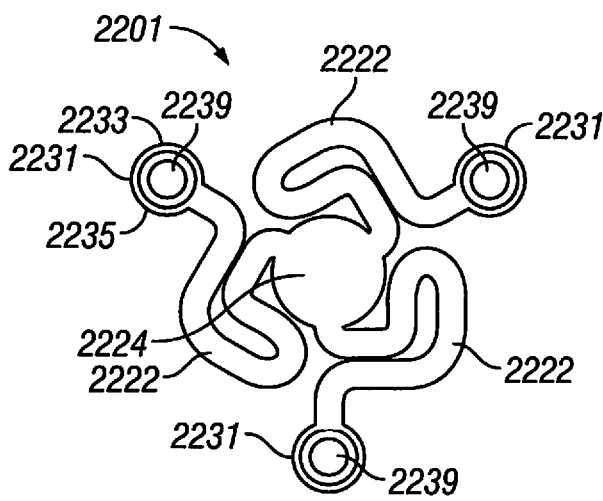
Figure 12D:
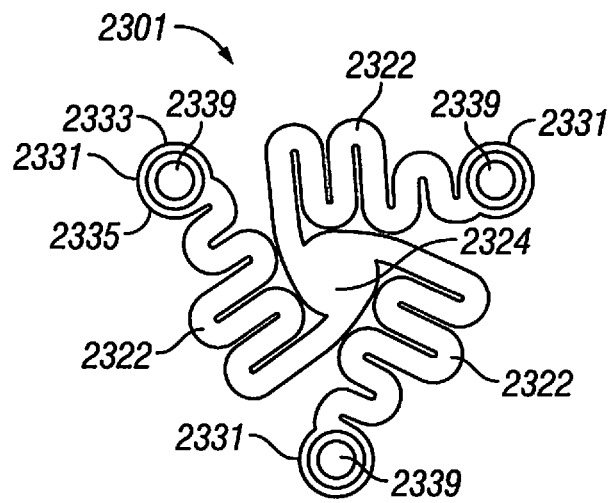

In the embodied bur hole covers shown in FIGS. 12C and 12D the covers 2201 and 2301 respectively each have thinner arms 2222, 2322 than those shown in FIGS. 12A and B and therefore the arms 2222 and 2322 require more bends and switchbacks to create enough surface area to substantially cover the bur hole.

Figure 12E:
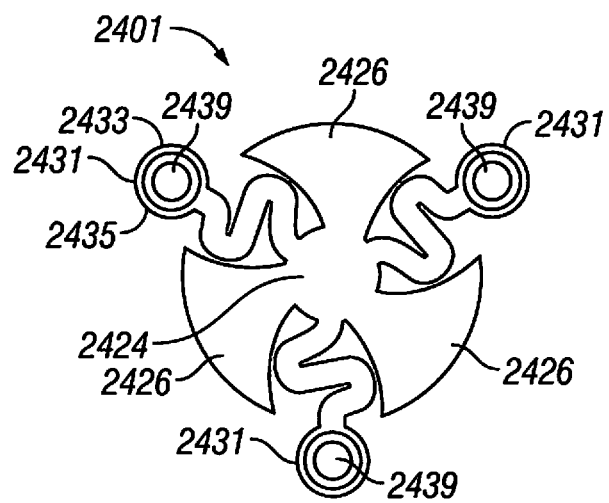

In the embodied bur hole cover shown in FIG. 12E the cover 2401 includes in addition to the center cover portion 2424 arms 2422 and wings 2431, a additional surface plates 2426 which are provided to further cover a bur hole 40 (not shown).

Figure 13A:
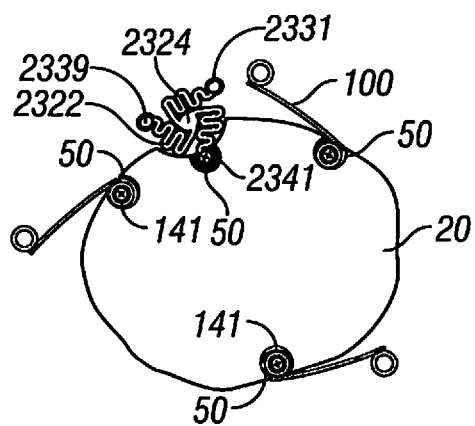
FIG. 13A shows the cranial flap with embodied cranial plates and an embodied bur hole cover attached.
Figure 13B:
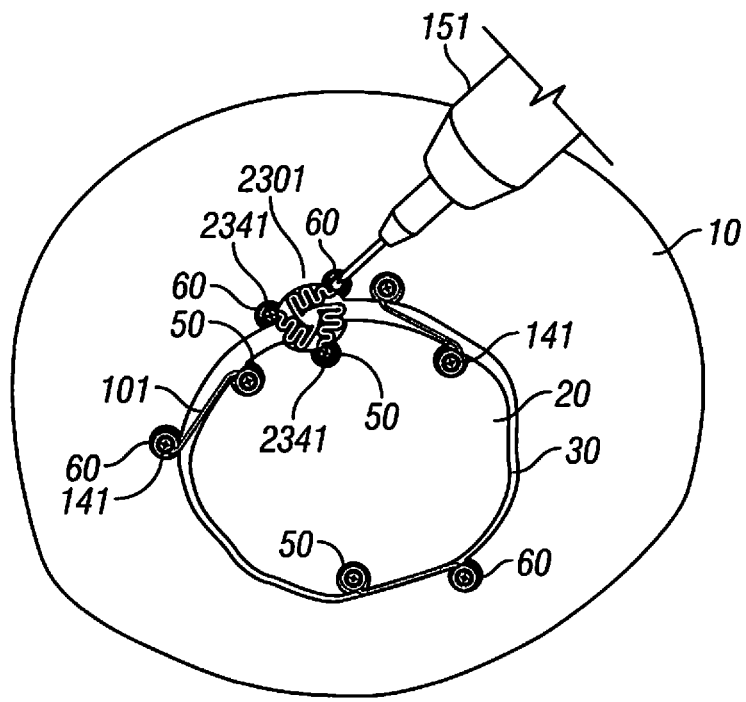
FIG. 13B shows the cranial flap placed back into the cranial opening and being resecured with embodied cranial plates and bur hole covers.
Figure 13C:
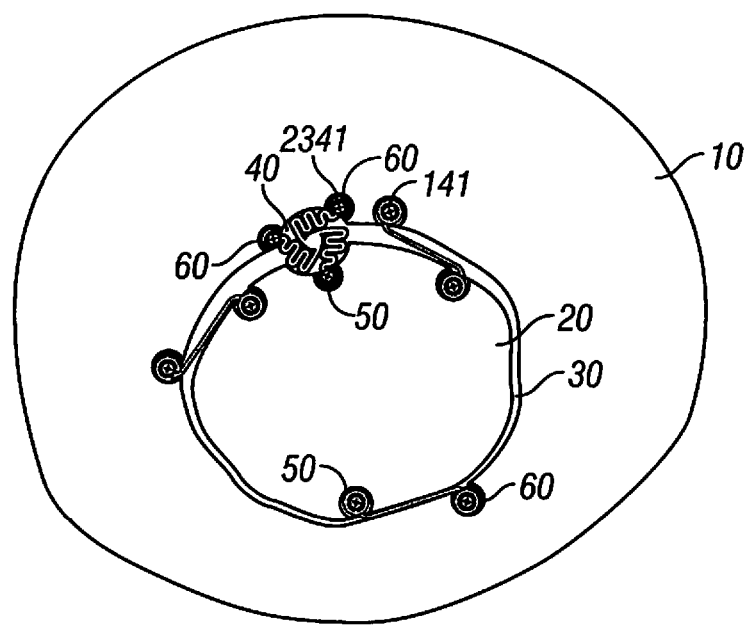
FIG. 13C shows the completed cranial closure with embodied cranial plates and bur hole covers.

A demonstration of the application of an embodied bur hole cover 2301 into a bur hole 40 where the cranial bone flap 20 is centered compared to the outlying cranium 30 is shown in FIG. 13 which is the same as FIG. 4 previously described for the cranial plate devices but now includes the addition of a bur hole cover embodiment. FIG. 13A demonstrates how one fixation wing 2331 of a bur hole cover 2301 is first placed into a cranial flap wing recess 50 which has been cut away to provide a specific placement of the fixation wing 2331 and is adhered to the cranial bone flap 20, with fixation screws 2341. FIG. 13B demonstrates the step wherein the cranial flap 20 is oriented back within the cranium 10, using the matching sides of one or more bur holes 40 to provide proper orientation and the bur hole cover 2301 is placed within the bur hole 40, and the other two fixation wings 2331 are placed into the cranium wing recesses 60 which have been cut away to provide a specific placement for the fixation wings 2331 and are adhered to the cranium 10 with fixation screws 2341. FIG. 13C demonstrates how the finished procedure appears, wherein a plurality of cranial plates 101 are positioned such that the keel 111 of each plate resides within the kerf 30, and that the fixation wings 131 for each plate 101 are recessed within cranial flap wing recesses 50 or cranium wing recesses 60 such that one wing 131 from each plate 101 is recessed 50 and attached to the cranial flap 20 and the other wing 131 from each plate 101 is recessed 60 and attached to the cranium 10 with fixation screws 141 and additionally the bur hole cover 2301 substantially covers the bur hole 40 and that the fixation wings 2331 for the bur hole cover 2301 are recessed within cranial flap wing recesses 50 or cranium wing recesses 60 such that one wing 2331 from the bur hole cover 2301 is recessed 50 and attached to the cranial flap 20 and the other two wings 2331 are recessed 60 and attached to the cranium 10 with fixation screws 2341.

Figure 14:
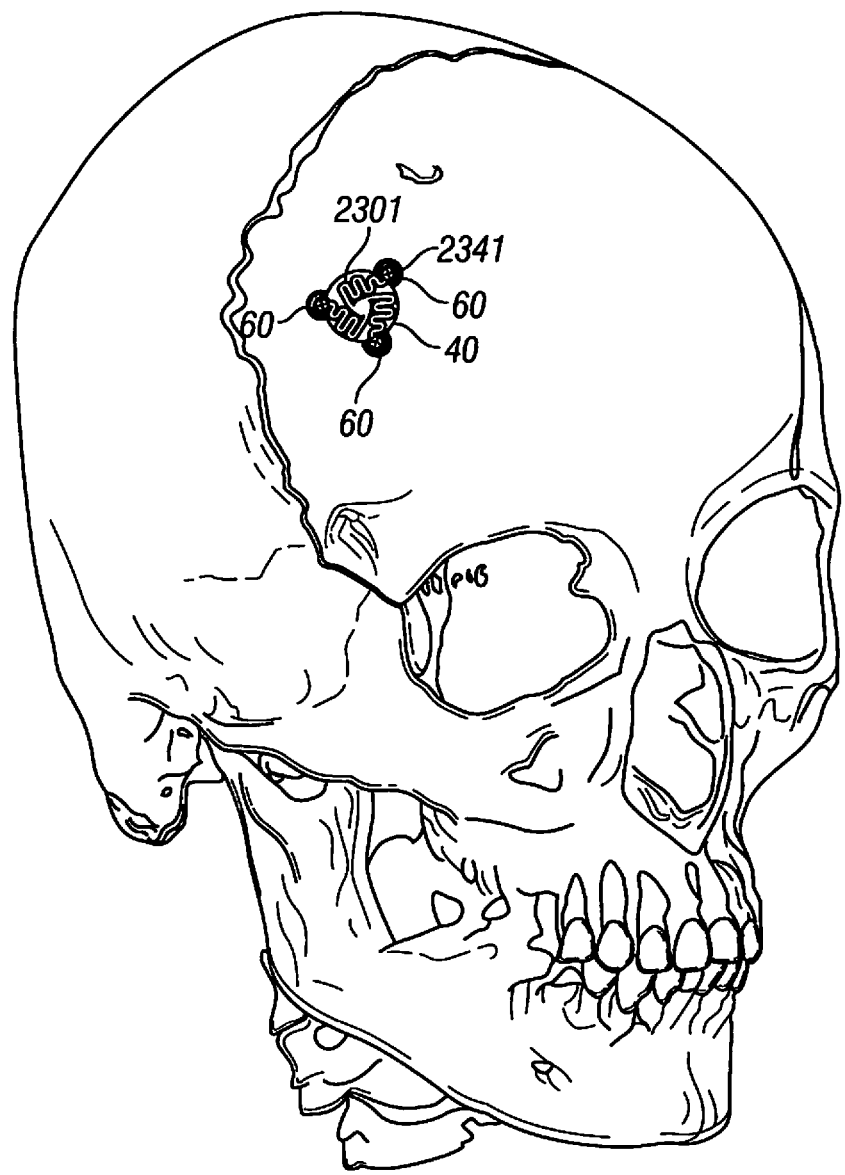
FIG. 14 is a side perspective view of the cranium and an embodied bur hole cover after attachment.

An additional demonstration of the application of an embodied bur hole cover 2301 into a bur hole 40 is shown in FIG. 14. In this application a bur hole 40 was drilled for surgical access which did not require a further cutting away of bone or the creation of a cranial flap 20. A bur hole cover 2301 is into the bur hole 40, the proposed placement of the attachment wings 2331 is marked on the cranium 30 with an awl and three cranium wing recesses 60 are cut away to provide specific placements for each of the three fixation wings 2331 which are adhered to the cranium 30, with fixation screws 2341.

The following examples are intended to illustrate but not limit the invention.

Example 1

Cranial Plating Device Design Variations

The kerf cranial closure device contemplated will feature many of the following properties which may optimize cranial closure performance:

1) The design is intended to specifically close the bony defect made in the skull by any of the common commercially available craniotomes, known as the kerf;
2) The keel portion of the cranial plate shall reside within the kerf;
3) The cranial plate fixation wings shall be on opposing sides of each other in relation to the keel;
4) The cranial plate fixation wings shall have a tapered fixation aperture which allows for the placement of a tapered fixation screw to reside flush within the cranial plate wing and allows for the thread of the fixation screw to secure into the cranium and flap;
5) The keel portion should be flexible or bendable, and/or manufactured with specific angles or curves to allow for the variability for closing various kerf configurations;
6) The keel portion may be solid or perforated;
7) The material contemplated is titanium but additional material such as other alloys of titanium, aluminum, stainless steel, tungsten, brass, cobalt, or copper; also nonmetallic materials such as poly (L0lactic acid), plastics such as polyethetketone (PEEK), or ceramics.

Example 2

Tooling Embodiments

The tooling system may comprise of an impression device which is a high-powered drill which consists of the cylindrical or disc-like bur (drill-bit) and the surrounding guide, the drill-bit is meant to be applied end on into the bone to make semicircular depression in the bone comprising a ⅗ to almost one whole circle that has a central point to allow the bit to bite bone at a precise spot this will also serve to create a pilot hole for screw when the plate is applied.

Another embodiment of the tooling system comprises the use of a guide the guide covers all the drill-bit except the last 0.4 to 0.7 mm the disc section the guide will prevent the drill-bit from cutting too deep when the guide tip rests on the bone, the impression made is at the proper depth to receive the plate. The guide has a two orientation posts or an orientation ridge, that are rested at the edge of the bone to assure that the impressions made at the edge of the bone are at the proper distance to allow plating.

Example 3

Exemplary Method of Using an Embodied Cranial Plating System

Cranial Defect

In the creation of a craniotomy, the bone is opened from its external surface to the level of the dura by placement of one or more bur holes, made either freehand with a high-speed drill or with a cranial perforator. The bur holes are connected with a high speed drill router (craniotome footplate attachment), which creates a trough in the bone, known as the kerf.

Closure of Cranium

At the conclusion of the intracranial part of the operation, the free bone flap is typically secured to the surrounding cranium with a fixation device in which pilot holes are drilled in the cranial flap and a plurality of fixation devices are attached to the cranial flap with screws inserted into the pilot holes, then the cranial flap is placed back into the cranial opening, and positions for attachment of the fixation devices is measured and marked with an awl, and a pilot hole is drilled into the cranium and the fixation devices are attached to the cranium with screws and the entire fixation device resides above the cranium surface. The typical fixation devices consist of titanium plates and screws (various manufacturers, e.g. Medtronic, Integra, Codman, Innovasis, Aesculap, W. Lorenz, etc. . . . ) or a disk/post device (Rapid Flap, CranioFix, others) which are all secured on the outer surface of the cranium and cranial plate.

Application of a Reduced Profile Cranial Plating System

Example 3a

Application of a Reduced Profile Cranial Plating System Using Current Techniques A reduced profile cranial plating system may be created merely by securing an embodied cranial plate device. Because the keel portion (a substantial portion of the entire device) resides within the kerf, there is much less plating device protruding over the surface of the cranium. Only the two affixation wings protrude. The cranial plating system in this application is applied just like any of the other standard fixation plates. One or more cranial plates are attached to the cranial flap at one affixation wing, the flap is placed back within the cranium space and the cranium is marked where the second affixation wing should be secured, a pilot hole is drilled and the plates are attached to the cranium.

Example 3b

Application of Inset Cranial Plate, Using Freehand Perforator or Drill to Partially or Fully Inset Wings of Cranial Plate A surgical drill is used to sculpt the surface of the bone to correspond to the shape of the wing using a round or straight bit. The plate is then inset into the trough cut by the drill into the bone flap and affixed with screws. Corresponding troughs are cut into the edges of the cranium to accommodate the wings, and the wings are then affixed to the cranium with screws.

Example 3c

Application of Inset Cranial Plate, Using Specialized Tooling to Inset Wings of Cranial Plate with a Higher Level of Precision Features a process of impressing then plating comprising the following steps: 1. A special drill bit makes an inset ¾ to ⅚ impression into the cranial flap at 3-4 or more fixation points 2. The resulting depression and bone thickness is equal to or slightly greater than the plate. 3. The cranial flap is plated at each inset point with fixation screws. 4. When placed into the kerf the plate has some spring or tension to it. 5. The plate is lined up with the cranium and corresponding holes are marked with an awl. 6. The bone flap is removed while matching insets are made in the cranium with the specialized drill tool. 7. The bone flap is inserted and plated into place.

Example 4

Bur Hole Cover Device Design Variations

The bur hole cover device contemplated will feature many of the following properties which may optimize cranial closure performance:

1) The design is intended to specifically close the bony defect made in the skull by any of the common commercially available bur hole cutters;

2) The center portion and arms of the bur hole cover shall comprise enough surface area to substantially cover the bur hole;

3) The bur hole cover fixation wings shall be spaced substantially equidistant from each other around a perimeter of the device;

4) The bur hole cover fixation wings shall be located at the distal ends of the arms which extend from the center portion;

5) The bur hole cover device is a unitary body, and the device is secured to the cranium or cranial flap with independent fixation sources selected from screws, tacks, rivets, or wires;

6) The bur hole cover device may comprise a center cover portion chosen from a substantially solid surface, or a perforated surface;

7) The arms of the bur hole cover device may be capable of being flexed or bent so as to enable an alignment with each wing and a placement hole drilled into the cranium or cranial flap;

8) The arms of the bur hole cover device may zigzag, loop or serpentine in order to increase surface area coverage for the bur hole, and allow for the arms to be flexed into a position so that the attached wings may be secured to the cranium or cranial plate without requiring precise placement of placement holes 9) The bur hole cover fixation wings shall have a tapered fixation aperture which allows for the placement of a tapered fixation screw to reside flush within the bur hole cover wing and allows for the thread of the fixation screw to secure into the cranium and flap;

10) The material contemplated is titanium but additional material such as other alloys of titanium, aluminum, stainless steel, tungsten, brass, cobalt, or copper; also nonmetallic materials such as poly (L0lactic acid), plastics such as polyethetketone (PEEK), or ceramics.

Application of a Reduced Profile Bur Hole Cover

Example 4a

Application of an Inset Bur Hole Cover, for Covering a Bur Hole Using Specialized Tooling to Inset Wings of Bur Hole Cover with a Higher Level of Precision Features a process of impressing then plating comprising the following steps: 1. The 3 fixation wings are lined up with the cranium and corresponding holes are marked with an awl. 2. A special drill bit makes an inset ¾ to ⅚ impression into the cranium at 3 fixation points 3. The resulting depression and bone thickness is equal to or slightly greater than the bur hole cover. 4. When placed into the bur hole the arms of the bur hole cover has some flexibility to it to allow the user to manipulate the fixation wings into the predrilled fixation points. 5. The arms of the bur hole cover are secured at each inset point with fixation screws.

Example 4b

Application of an Inset Bur Hole Cover, Using Specialized Tooling to Inset Wings of Bur Hole Cover with a Higher Level of Precision This procedure is typically done in concert with Example 3c above and features a process of impressing then plating comprising the following steps: 1. A special drill bit makes an inset ¾ to ⅚ impression into the cranial flap at 1 or 2 fixation points for each bur hole cover 2. The resulting depression and bone thickness is equal to or slightly greater than the bur hole cover. 3. The cranial flap is secured at each inset point with fixation screws. 4. When placed into the bur hole the arms of the bur hole cover has some flexibility to it. 5. The other 1 or 2 fixation wings are lined up with the cranium and corresponding holes are marked with an awl. 6. The bone flap is removed while insets are made in the cranium with the specialized drill tool. 7. Additional cranial plates or bur hole The bone flap is inserted and secured into place.

Although the invention has been described with reference to the above example, it will be understood that modifications and variations are encompassed within the spirit and scope of the invention. Accordingly, the invention is limited only by the following claims.

What is claimed is:

1. A device for use in craniotomies comprising: a cranial plate comprising two wings and a keel; wherein one of the two wings is configured to be affixed on an outer surface of a cranial flap and the other wing is configured to be affixed on an outer surface of a cranium surrounding the cranial flap and the keel is configured to reside in a kerf (gap) left by a craniotome blade;

wherein the two wings are located at opposing ends and opposing sides of the keel;

wherein the keel is attached to the wings at keel wing attachment points and is located below the two wings; and wherein the keel has a length of at least 6 mm and is configured such that part of the keel resides within the kerf to create a scaffold for bone regrowth; and wherein the cranial plate is of unitary one piece construction.

2. The device according to claim 1; wherein the two wings are located at least 6 mm apart from each other at the opposing ends of the keel.

3. The device according to claim 1; wherein the cranial plate is configured to be secured to the cranium with independent fixation sources selected from screws, tacks, rivets, or wires.

4. The device according to claim 1; wherein each wing comprises a tapered inset hole paired with a tapered fixation screw, wherein each tapered fixation screw is configured to secure the device to the cranium or cranial flap.

5. The device according to claim 1; wherein the keel is chosen from a solid surface, or a perforated surface.

6. The device according to claim 1 wherein the keel is straight, angled or curved.

7. The device according to claim 1, wherein the keel is capable of being flexed or bent.

8. The device according to claim 1, wherein each of the two wings has a diameter ranging from 2 mm to 8 mm with a hole having a diameter ranging from 1 mm to 4 mm and each of the two wings has a depth ranging from 0.2 mm to 2.0 mm.

9. The device according to claim 1, wherein the keel has a length ranging from 6 mm to 20 mm; the keel has a depth ranging from 1 mm to 10 mm; and the keel has a width ranging from 0.3 mm to 3.0 mm.

10. The device according to claim 1, wherein the keel is coated with a medicament or a medicament is affixed to the keel, and wherein the medicament may comprise of bone growth proteins, antibiotics, antibacterial agents and/or antiseptic agents in order to prevent bone flap infection and/or assist with bone regrowth.

11. The device according to claim 1, wherein the keel is perforated or opened so that the keel structure is capable of providing a scaffold for bone regrowth into the kerf.

12. The device according to claim 1, wherein the two wings are configured to be affixed within recesses formed in the outer surfaces of the cranial flap and cranium such that the wings do not protrude outside of said recesses of the cranial flap and cranium.

* * * * *